US012590119B2

(12) United States Patent
Sillard et al.

(10) Patent No.: US 12,590,119 B2
(45) Date of Patent: Mar. 31, 2026

(54) PEPTIDE SYNTHESIS AND SYSTEM THEREOF

(71) Applicant: PEPTISYSTEMS AB, Uppsala (SE)

(72) Inventors: Rannar Sillard, Enebyberg (SE); Mats Israelsson, Uppsala (SE); Ulf Tedebark, Järfälla (SE); Lars Holmberg, Uppsala (SE)

(73) Assignee: PEPTISYSTEMS AB, Uppsala (SE)

( * ) Notice: Subject to any disclaimer, the term of this patent is extended or adjusted under 35 U.S.C. 154(b) by 711 days.

(21) Appl. No.: 17/906,403

(22) PCT Filed: Mar. 16, 2021

(86) PCT No.: PCT/SE2021/050229
§ 371 (c)(1),
(2) Date: Sep. 15, 2022

(87) PCT Pub. No.: WO2021/188032
PCT Pub. Date: Sep. 23, 2021

(65) Prior Publication Data
US 2023/0135860 A1 May 4, 2023

(30) Foreign Application Priority Data
Mar. 17, 2020 (SE) .................................... 2050293-6

(51) Int. Cl.
*C07K 1/107* (2006.01)
*B01J 8/00* (2006.01)
*B01J 8/04* (2006.01)
*C07K 1/02* (2006.01)

(52) U.S. Cl.
CPC ............. *C07K 1/1075* (2013.01); *B01J 8/001* (2013.01); *B01J 8/0403* (2013.01); *B01J 8/0492* (2013.01); *B01J 8/0496* (2013.01); *C07K 1/02* (2013.01); *B01J 2208/00061* (2013.01); *B01J 2208/00477* (2013.01); *B01J 2208/00628* (2013.01); *B01J 2208/00849* (2013.01)

(58) Field of Classification Search
None
See application file for complete search history.

(56) References Cited

U.S. PATENT DOCUMENTS

| | | | |
|---|---|---|---|
| 4,192,798 A | 3/1980 | Verlander et al. | |
| 4,668,476 A | 5/1987 | Bridgham et al. | |
| 6,028,172 A | 2/2000 | Stepaniuk et al. | |
| 6,033,631 A * | 3/2000 | Zuckermann .......... | C07K 1/045 |
| | | | 422/135 |
| 7,902,488 B2 | 3/2011 | Collins et al. | |
| 9,169,287 B2 | 10/2015 | Simon et al. | |
| 10,981,947 B2 | 4/2021 | Olovsson et al. | |

| | | | |
|---|---|---|---|
| 2014/0275481 A1 | 9/2014 | Simon et al. | |
| 2017/0081358 A1 | 3/2017 | Thomas, III et al. | |
| 2018/0057525 A1 | 3/2018 | Simon et al. | |
| 2021/0094982 A1 | 4/2021 | Ludemann-Hombourger et al. | |

FOREIGN PATENT DOCUMENTS

| | | |
|---|---|---|
| JP | H07-089983 A | 4/1995 |
| JP | 2016-515114 A | 5/2016 |
| JP | 2017-512632 A | 5/2017 |
| JP | 2018-530543 A | 10/2018 |
| WO | 2016/205546 A1 | 12/2016 |

OTHER PUBLICATIONS

Office Action dated Jun. 3, 2025, issued in corresponding Japanese Patent Application No. 2024-094946.
Tedebark et al., "ÄKTATM oligopilotTM for Automated Solid Phase Peptide Synthesis", Proceedings of the 30th European Peptide Symposium, Helsinki, Finlandia Hall, 2008, article No. 3-06-104, p. 450-451.
Mijalis et al., "A fully automated flow-based approach for accelerated peptide synthesis", Nature Chemical Biology, vol. 13, No. 5, Feb. 28, 2017, pp. 464-468, XP055577197.
Mijalis et al., "A fully automated flow-based approach for accelerated peptide synthesis (Supplementary Information—pp. 1-20)", vol. 13, No. 5, Feb. 28, 2017, pp. 464-466, Retrieved from the Internet: URL: http://www.nature.com/articles/nchembio.2318, XP055813297.
Nissen et al., "Hot or not—the influence of elevated temperature and microwave irradiation on the solid phase synthesis of an affibody", Tetrahedron Letters, vol. 51, No. 48, Dec. 1, 2010, pp. 6216-6219, XP027447671.
International Search Report and Written Opinion dated Jun. 23, 2021, issued in corresponding International Patent Application No. PCT/SE2021/050229.
Lukas et al., "Solid-phase peptide synthesis under continuous-flow conditions", Proc. Natl. Acad. Sci. USA, May 1981, vol. 78, No. 5, pp. 2791-2795.
Office Action dated Mar. 13, 2023, issued in corresponding Swedish Patent Application No. 2050293-6.
Office Action dated Sep. 26, 2023, issued in corresponding Japanese Patent Application No. 2022-556278.
English translation of Notice of Reasons for Rejection issued in Japanese Patent Application No. 2024-094946 dated Dec. 2, 2025.
First Examination Report issued in co-pending Indian Patent Application No. 202227058305 dated Dec. 22, 2025.

* cited by examiner

*Primary Examiner* — Sergio Coffa
(74) *Attorney, Agent, or Firm* — Morgan, Lewis & Bockius LLP

(57) ABSTRACT

Processes and systems related to solid phase peptide synthesis are described. The processes include a flow-through process comprising cyclic addition of amino acids to a column packed with resin, wherein each cycle includes the combination of the amino acids with one or more reagents to provide an activated amino acid mixture, and wherein heating is applied to the amino acid(s) before they are passed through the column and wherein the amino acids are re-circulated at least once over the column packed with resin. Systems for such processes are also described.

18 Claims, 10 Drawing Sheets

PEPTIDE SYNTHESIS AND SYSTEM THEREOF

FIELD OF INVENTION

The present invention relates to processes and systems for solid state peptide synthesis.

INTRODUCTION

Peptides are short chains of amino acid residues linked by amide bonds, usually containing 2 to 50 amino acids. Amino acids are the basic building blocks for all living organisms and the precursors of both peptides and proteins. Chains of amino acid residues longer than 50 monomers are usually referred to as proteins. Peptides are highly interesting and widely used since they have many biological functions depending on their amino acid sequences and other structural characteristics. The world market for peptides is growing rapidly, mainly because of increasing application of peptides as pharmaceuticals for treatment of many kinds of diseases and as bioactive components in cosmetics. Additionally, application of peptides is expanding into new areas such as drug delivery, antibiotics, active components in medical devices, and uses in agriculture, such as insecticides, regulators of plant development, etc. Thus, the market demand for peptides is increasing and creating the need for producing them synthetically in large quantities. Therefore, new developments in the field are required to make peptide synthesis more efficient, cheaper and environmentally friendly.

Synthesis of peptides usually includes repeated steps of adding amino acid residues one by one to a growing peptide chain. As an alternative to adding single amino acids, peptides can also be added one by one to a growing peptide chain. Peptides can be synthesized in solution by liquid phase peptide synthesis (LPPS), by using solid-phase approach (solid phase peptide synthesis, SPPS) or by combining both methods, which is also known as convergent or hybrid technique. In SPPS the growing peptide chain is immobilized on a solid phase support usually at its C-terminus. In some cases, the N-terminus or amino acid sidechains can be immobilized to the resin. New amino acid residues are added by coupling reactions to the N-terminus. The amino acid sidechains and their N-terminal amino groups are usually chemically blocked by protecting groups to prevent unintended reactions. In each step the N-terminus of the growing peptide is selectively deprotected to allow for the addition of the next amino acid. Finally, the peptide is released from the solid support by chemical cleavage by breaking the chemical bond between the peptide and the support. Further handling of the peptide typically includes isolation followed by purification. During the cleavage process protecting groups are normally also removed from the amino acid sidechains. Though, this is not the case when a sidechain-protected peptide is required, typically in a convergent or hybrid approach.

SPPS may be carried out in e.g. a batch or a flow-through reactor. Batch reactors have become one of the most widely used techniques for synthesis of longer peptides. However, synthesis in batch reactors compared to flow-through technique involve disadvantages such as longer lead times for each coupling, more time-consuming optimization for scalability, and frequently, excess use of solvents and reagents due to limitations in Process Analytical Technology (PAT). Also, batch reactors lack the possibility for real-time monitoring of the progress of each step. Contrary to batch reactors, continuous liquid flow in the system allows for constant monitoring of the processes by using different kinds of detectors and sensors that can be connected in-line. A flow-through reactor generally has the advantage of faster kinetics, lower solvent and reagent consumption and it permits real-time monitoring of the reaction.

U.S. Pat. No. 9,169,287 B2 discloses a process for performing SPPS quickly and with high yield. The process comprises heating a stream of amino acids so that the temperature of the amino acids is increased by at least about 1° C., and exposing the heated amino acids to a plurality of peptides immobilized on a solid support, wherein the heating step is performed prior to and within about 30 seconds of exposing the heated amino acids to peptides.

Tedebark U. et al. in Proceedings of the $30^{th}$ European Peptide Symposium, Helsinki, Finlandia Hall, 2008 discloses a process and a system for automated SPPS. The system includes four pumps, a pre-activation chamber (including possibility for pre-activation temperature control), a column, a UV detector and a conductivity detector.

U.S. Pat. No. 7,902,488 B2 discloses an instrument and process for accelerated synthesis of peptides by a microwave assisted SPPS method. The instrument includes a microwave cavity, a microwave source in communication with the cavity, a column in the cavity formed of a microwave radiation transparent material, a solid phase peptide support resin in the column, respective filters for maintaining the solid support resin in the column, a first passageway for adding starting compositions to the column, a second passageway for removing compositions from the column, and a third passageway for circulating compositions from the column into the third passageway and back to the column.

U.S. Pat. No. 4,668,476 discloses an apparatus for automatically constructing a polypeptide of high purity, up to 50 amino acids in length, using only single couplings. The apparatus includes an activation system for receiving protected amino acids, one kind at a time, having a common vessel in which to activate each of the amino acids.

U.S. Pat. No. 6,028,172 discloses a solid phase synthesis reactor system and method of operating the reactor. The reactor system includes a basket rotatable about an axis within a housing and a receiver which delivers fluid to, and collects fluid from, the housing. The basket has a perforate side wall against which a resin cake for the peptide synthesis is formed. The reactor and the receiver form a loop or circuit through which solutions are circulated.

In the prior art there is still a need for an improved SPPS process and system in terms of process efficiency, performance, impact on the environment, and to meet the requirements on sustainable peptide production. For example, there is a need for an improved SPPS process and system that allows to use a reduced amount of amino acid equivalents during the synthesis and reduced solvent use during washing steps. Another need in the area is related to the scalability of SPPS processes from lab scale to pilot- and process scale, and finally to commercial manufacturing.

SUMMARY

SPPS processes and associated systems are generally described.

In one aspect of the invention there is a flow-through process for solid phase peptide synthesis (SPPS) including cyclic addition of at least one amino acid to a column packed with resin, wherein each cycle includes the combination of amino acid(s) with one or more reagents to provide an amino acid mixture which is passed through the column, which method comprises that heating is applied to the amino acid mixture before they are passed through the column, the amino acid mixture is passed through the column packed with resin, and the amino acid mixture is recirculated at least once over the column packed with resin, whereby in each cycle, peptides are synthesized by linking at least one amino acid from the mixture to at least one amino acid immobilized to the resin.

In another aspect of the invention, there is a system for flow-through solid phase peptide synthesis (SPPS), wherein the system comprises at least one column packed with resin, at least one pump, reservoirs for amino acids and reagents, at least one temperature regulating device, at least one temperature sensor, at least one detector, and at least one gas (bubble) detector, wherein tubing connects the reservoirs to the column, and valves are arranged to direct the flow in the system. The processor is in communicative connection at least with the pump, the valves, the detector and the temperature regulating device.

In one example of the invention, there is a system according to the invention that comprises valves, flow re-directing valves, a temperature regulating device bypass, a column bypass, a waste outlet, and a separately defined mixing chamber. The first valve is arranged downstream and in fluid communication with the reservoir, and in fluid communication with the first flow re-directing valve arranged downstream the first valve. The first flow re-directing valve is in fluid communication with the pump. The second flow re-directing valve is arranged downstream and in fluid communication the first flow re-directing valve, the second flow re-directing valve is in fluid communication with the temperature regulating device and with the temperature regulating device bypass. The temperature regulating device is arranged downstream and in fluid communication with the second flow re-directing valve. The third flow re-directing valve is arranged downstream and in fluid communication with the temperature regulating device. The second valve is arranged downstream and in fluid communication with the third flow re-directing valve, the second valve is arranged upstream and in fluid communication with the column bypass and the column. The column is arranged upstream and in fluid communication with the third valve, the third valve is downstream and in fluid communication with the column bypass. The third valve is arranged upstream and in fluid communication with the detector. The detector is arranged downstream the fourth valve, the fourth valve is arranged in fluid communication with the waste outlet and the separately defined mixing chamber, and downstream and in fluid communication with the fifth valve. The fifth valve is arranged in fluid communication with the separately defined mixing chamber. The gas bubble detector is arranged upstream and in fluid communication with the separately defined mixing chamber, and downstream the fifth valve. The fifth valve is arranged downstream and in fluid communication with the first valve. The tubings connects the valves, the flow re-directing valves, the reservoir, the column, the temperature regulating device, the pump, the temperature sensor, the detector, the gas bubble detector, the waste outlet, and the separately defined mixing chamber to each other. The processor is in communicative communication with the valves, the flow re-directing valves, the temperature regulating device, the pump, the temperature sensor, the detector, and the gas bubble detector.

In one example of the invention there is a method for performing flow-through solid phase peptide synthesis using a system according to the invention, the method comprising the steps of:

Mixing step: the system is arranged to arrange the first valve so that synthesis liquid comprising amino acids, reagents, solvent(s), and possible additives flow from the reservoir into the system. The system is arranged to flow the synthesis liquid to separately defined mixing chamber via the temperature regulating device bypass and the column bypass by controlling at least the first flow redirecting valve, the second flow-redirecting valve, the third flow re-directing valve, the second valve, the third valve, the fourth valve, the fifth valve.

Activation step: the separately defined mixing chamber is arranged to activate the amino acids that entered the separately defined mixing chamber in the mixing step. The detector is arranged to monitor the activation step.

Coupling step: the system is arranged to pass the heated amino acids over the column by controlling at least the second valve and the third valve. The system is arranged to re-circulate the amino acids over the column at least once by arranging the valves, and the flow re-directing valves.

Capping step: the system is arranged to provide a capping solution to the column by controlling at least the first valve, the second valve, the third valve, the first flow re-directing valve and the second flow re-directing valve.

Deblocking step: the system is arranged to provide a de-blocking solution from the reservoir to the column by arranging at least the first valve, the second valve, the third valve, the first flow redirecting valve and the second flow re-directing valve.

The mixing, activation, coupling, capping and deblocking steps are repeated at least once. At least a washing step is performed prior to or after the capping step. The processor is arranged to be in communicative communication with and control the valves, the pump, the detector, the gas bubble detector, the flow re-directing valves, and the temperature regulator device.

Below, the invention will be described in more details by way of non-limiting examples and depending claims.

DEFINITIONS

Figure 1:
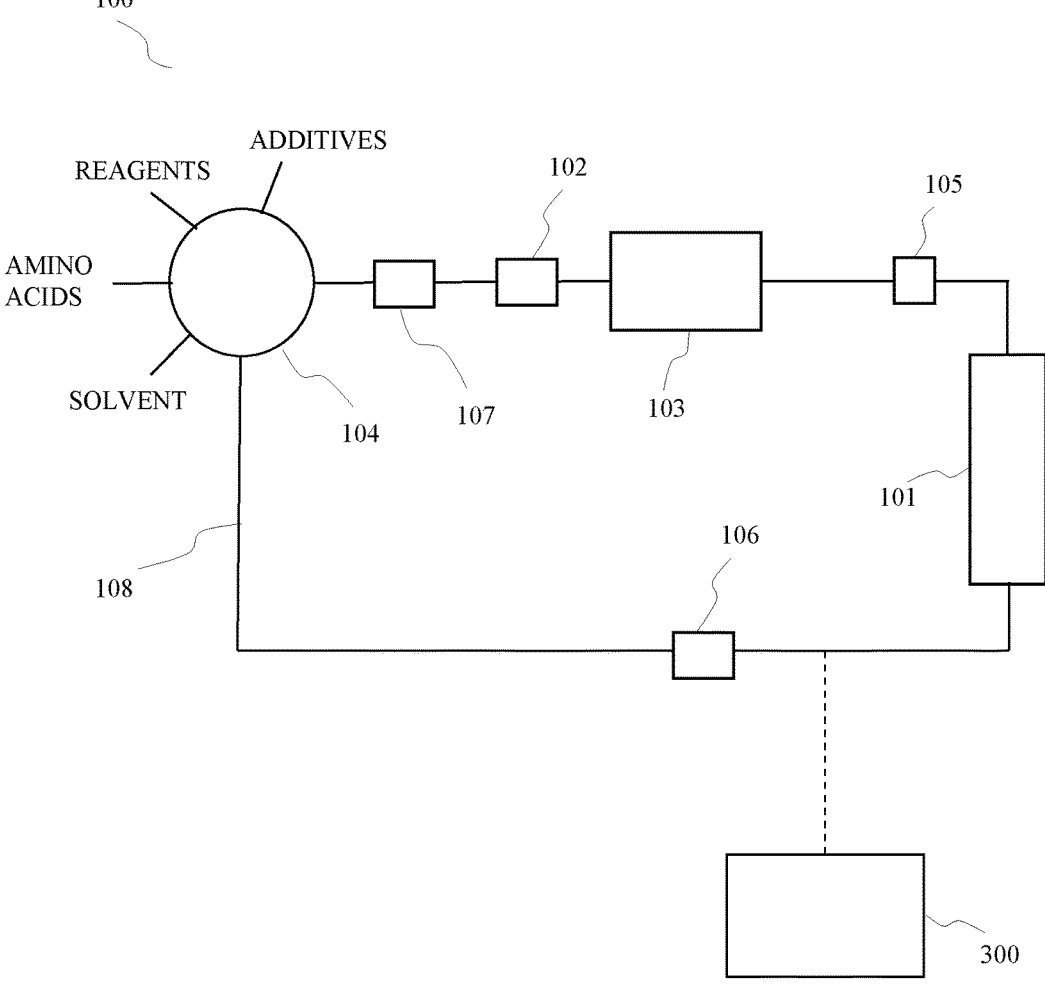
FIG. 1. is a schematic illustration of one example of a system according to the invention.

In the present patent application, the following terms are used and defined throughout the description and claims:

'amino acid' is used in its conventional meaning in the field and refers to an organic compound that contains at least one amino group (e.g. $-NH_2$, $-RNH$), and one carboxyl group (e.g. —COOH, —COR' where R'—OR, NRH, or —NR₂) or carboxyl derivative (e.g. —COOR);

'peptide' is used in its conventional meaning in the field and refers to two or more amino acids (the same or different) that are linked via an amide bond;

'amino acid mixture' as used herein is a liquid including amino acid(s) as well as reagent(s) as used herein, wherein the 'amino acid' may be modified or non-modified, and optionally pre-activated, which amino acid mixture may also include peptides;

contact with 'growing peptide' includes a contact with a peptide chain or with an amino acid immobilized on resin and the first step of adding an amino acid to a resin;

'SPPS' is the abbreviation for Solid Phase Peptide Synthesis and used in its conventional meaning in the field;

'reagent' is used in the meaning of coupling reagents, de-blocking reagents, additives, bases, and other reagents used for synthesis;

'linearly scalable' have the meaning of a synthesis process wherein the synthesis conditions in a smaller or larger scale can be transferred to an alternative size of scale giving a similar synthesis outcome;

'PAT' is an abbreviation for Process Analytical Technology and used in its conventional meaning in the field;

'CPP' is an abbreviation for Critical Process Parameters and used in its conventional meaning in the field;

'CQA' is an abbreviation for Critical Quality Attributes and used in its conventional meaning in the field;

'conditional threshold' is used in the meaning of a pre-defined value of at least one parameter set in the control software to allow the previous step(s) to be ended and the subsequent step to start;

'flow through' peptide synthesis refers to a peptide synthesis process wherein, as opposed to a batch process, the synthesis liquid comprising reagents pass through the column; and 're-circulation' peptide synthesis refers to a process that is a type of flow-through process wherein the synthesis liquid is re-circulated at least once in the system so that it pass over the column at least twice 'handle' is used in its conventional meaning in the field and refers to any functional group on a resin used for attachment of any derivative to facilitate solid-phase synthesis of any derivative, non-limiting examples include a linker attachment to a solid support/resin e.g. amine, the next e.g. amino acid to a solid support/resin linker handle.

DETAILED DESCRIPTION

SPPS processes and associated systems are generally described. SPPS is a known process to produce peptides by adding amino acid residues to an amino acid or peptide immobilized on a solid support (resin).

In a first aspect of the invention there is a flow-through process for solid phase peptide synthesis (SPPS) including cyclic addition of at least one amino acid to a column packed with resin, wherein each cycle includes the combination of amino acid(s) with one or more reagents to provide an amino acid mixture which is passed through the column. The method comprises that heating is applied to the amino acid mixture before they are passed through the column packed with resin, that the amino acid mixture is passed through the column packed with resin, whereby in each cycle, peptides are synthesized by linking at least one amino acid from the mixture to at least one amino acid immobilized to the resin. In one example of the first aspect the amino acid mixture is re-circulated at least once over the column packed with resin. In one example of the first aspect the amino acid(s) are combined with said reagent(s) in a separately defined mixing chamber. In one example of the first aspect the amino acid(s) are combined with said reagent(s) in the tubing of the system. In one example of the first aspect the amino acid(s) are combined with said reagent(s) in the column packed with resin.

In the first aspect of the invention the SPPS process comprises cycles, wherein amino acid residues are added to solid support (resin) or an immobilized amino acid or an immobilized peptide. As understood by persons skilled in the art the amino acid(s) that are added to the immobilized amino acid or peptide may be a single amino acid, or a terminal of a peptide of suitable size. Thus, the present invention is not limited to adding single amino acids in the synthesis.

In a process according to the invention amino acids and peptides are immobilized on a porous solid support, such as a support comprised of resin particles packed as a bed in a column. Hence, the invention relates to a process using a packed bed. Any suitable type of resin may be used to immobilize the peptides, such as microporous resins, mesoporous resins, and macroporous resins. Specifically, such resins may be prepared from synthetic polymers, such as crosslinked polymers, which e.g may be any polymer selected from the group consisting of polystyrene, such as styrene-DVB, polyethylene glycol (PEG), polyacrylate, and polyacrylamine; or any combinations thereof; or natural polymers, which may be selected from the group consisting of agarose; cellulose and carbohydrates. Advantageously, the process according to the invention uses a bed packed with porous particles comprised of polystyrene crosslinked with divinylbenzene. Such particles are readily available from commercial sources, and the skilled person is capable of providing an appropriately packed bed using standard methods.

As the skilled person will appreciate, an "amino acid" as used herein includes a single amino acid as well as an amino acid which has been coupled to one or more other entities. Thus, unless differently specified, an "amino acid" as used herein may e.g. be part of a peptide, or of a small protein. Each cycle comprises at least the following steps:

Combination step: amino acids or peptides are combined with one or more reagents. Examples of reagents are known to a person skilled in the art. Examples can also be found in various literature such as in "Fmoc Solid Phase Peptide Synthesis—A practical approach" Chan W. C., and White P. D. (eds.), Oxford University Press, 2000. The combination may occur either in a separate mixing chamber or in the tubing of the system or directly in the column. The amino acids together with one or more reagents are heated inside the system before they are passed through the column.

Activation step. The amino acids, or peptides, can be activated inside the SPPS system, for example, in the following non-limiting ways:

a) by pre-activation, i.e. the amino acids are activated in a separately defined mixing chamber; or b) by in-line activation, i.e. the amino acids are activated in the tubings of the system. The in-line activation may occur before reaching the column or inside the column.

The amino acids can also be purchased already activated and in such case the already activated amino acids are added to the system and optionally combined with one or several reagents in the mixing chamber or in-line. Optionally can additive(s) be added at any time to the already activated amino acids, for example to facilitate coupling.

Coupling step. After the activation step, which may occur either in the mixing chamber or in-line, the activated amino acids or peptides are passed through the column and are exposed to the solid support, which may carry one already immobilized amino acid or an immobilized peptide. The activated amino acids or peptides can be passed through the column or recirculated through the column at least once. They can also be recirculated for several times, where the number of times is determined by the liquid flowrate and the recirculation time. Other kinds of coupling reactions may also be carried out such as condensation, click-like conjugations, native chemical ligation or coupling reactions using enzymes, etc. as considered suitable by the persons skilled in the art.

Passing the liquid interchangeably from either end of the column may be beneficial in the coupling step, where it may facilitate e.g. to maintain uniform temperature in the column, repacking of column resin etc.

Capping step. After completion of the coupling step any unreacted fraction of e.g. the N-terminal amino groups on the growing peptide can be capped to block these from unwanted reactions. The process of capping may comprise passing a capping solution of predefined concentration through the column at a predefined flow rate. The process may be carried out by passing the capping solution through the column directly after the coupling step prior to washing, or by having a washing step performed after the coupling step and the capping step after the washing.

Removal of waste. A solvent is passed through the column to wash out any excess amino acids, reagents and soluble by-products after the coupling step or to wash out the excess capping reagent including by-products after the capping step. The washing may be performed using displacement technique. Washing of the column is monitored in-line and in real-time and continued until a conditional threshold has been reached. Such threshold can be determined by a person skilled in the art. The monitor may be a UV/VIS monitor/detector or any other suitable kind of detector.

Removal of blocking groups from the solid support and/or the N-terminus of the growing peptide. The process may additionally comprise deblocking reactions to remove blocking/protecting groups directly from the linkers on the solid support in the beginning of the process and removal of blocking/protecting groups from the N-terminus or from other functional groups of the immobilized amino acid or the immobilized growing peptide. The blocking groups involved may be e.g. Fmoc-groups or any other blocking/protecting group known for those skilled in the art. For removal of the blocking groups defined reagent solutions at predetermined concentrations may be passed through the column at predetermined flowrates. The process may include heating of said reagent solutions. The process may release derivatives that can be real-time monitored in-line by a detector, e.g. a UV/VIS detector. The process may be monitored and controlled by a feedback mechanism, where the total volume of the reagent is determined by the feedback from a detector and when conditional threshold(s) has/have been reached.

Removal of blocking groups from amino acid side chains and further reactions with the immobilized peptide. During the synthesis process reactive side-groups of the immobilized growing peptide may be temporarily blocked. In such case the process may further comprise steps, wherein any of these side-groups are selectively deblocked. The selectively deblocked groups can then be used for further chemical synthesis similarly as described in the coupling step or by using other conditions, reagents and reactions identified by persons skilled in the art. Different reagents and solvents are passed through the column for such deblocking and further chemical reactions. Selective chemical reactions may also be carried out without prior need for deblocking.

At the end of the process, when the desired peptide sequence/derivative has been synthesized the crude peptide is cleaved off from the resin, and any protecting groups may be removed. The peptide may be purified using purification techniques known to persons skilled in the art, such as reversed phase HPLC, for example.

In the present context heating may mean a heating of 1° C., or 3° C., or 5° C., or such that the amino acid mixture is heated to a temperature of e.g. 43° C., or 50° C., or 60° C., or 70° C. A person skilled in the art can determine the heating level depending on the reaction, type(s) of amino acids, type(s) of reagents etc.

In one example of the first aspect the amino acids and reagents are combined by recirculation of liquids in the system, or in the column. Effective mixing is beneficial for all chemical reactions such as pre-activation of amino acids, coupling reactions etc. Effective mixing may be achieved by several non-limiting techniques such as by gas bubbling through a mixing chamber, in-line mixing of at least two liquid streams, etc. A mixing loop may or may not include the column.

In one example of the first aspect the number of equivalents of amino acids is ≤3, such as ≤2.

In an example of the first aspect the heated amino acid mixture is passed through the column at a flow rate, and in a volume that allow for their contact with at least 99% of the immobilized and growing peptides.

In the SPPS process the mixture comprising amino acids is recirculated over the column. Recirculation means that the amino acid mixture that has passed the column once is transported through the tubing of the SPPS system and enters the column again at least one more time. Different reagents and additives may be added to the recirculation liquid. The recirculation may be repeated at least once. The recirculation facilitates the use of a less excess of amino acids than is required in the case of a single passage. The number of equivalents of amino acids may be ≤4, or ≤3, or ≤2, and an amino acid is added to at least about 99%, or to at least about 95%, of the immobilized peptides. A person skilled in the art can determine the concentration of amino acids in the recirculation liquid depending on reaction, expected outcome, type(s) of amino acids, type(s) of reagents, etc. The use of a lesser excess of amino acid equivalents than in conventional SPPS processes is not only more cost efficient but also more environmentally friendly since it saves both reagent(s) and solvent(s) and reduces waste.

In an example of the first aspect the mixing chamber is emptied and cleaned between the cycles and the progress of the cleaning is monitored by a UV/visible/IR light detector or a conductivity detector or both.

The mixing chamber is emptied and cleaned between the cycles using dilution with a solvent and the progress of the cleaning is monitored using a UV/Vis detector, a conductivity detector or both. Also, other detectors may be included. The emptying and cleaning of the mixing chamber may be performed while the resin in the column is being cleaned either running the two processes independently and simultaneously or by passing the cleaning solvent first through one of these units and then through the other (i.e. first through the mixing chamber and then through the column or vice versa).

Washing of the mixing chamber can be combined with washing the column by passing a washing solvent e.g. DMF sequentially first to the mixing chamber and thereafter through the column.

In an example of the first aspect the reagents comprise at least one activating agent and the amino acids are in-line activated in the tubing or in the column.

The amino acids may be in-line activated in the tubing, or in the column, or in a combination of both.

In another example of the first aspect the reagents comprise at least one activating agent and the amino acids are pre-activated in the mixing chamber while the column resin is being prepared for the next building block. The outflow of the mixing chamber may be monitored using gas bubble detection.

As described above, the amino acids used in the synthesis can be activated inside the SPPS system in two different ways:

pre-activated, the amino acids are activated in the separately defined mixing chamber, prior to being added to the resin. When the amino acids have been pre-activated in the mixing chamber, the emptying of the mixing chamber can be monitored by gas bubble detection; or in-line activated, the amino acids are activated in the tubing of the system and/or possibly inside the column, in both cases in the absence of a separate mixing chamber. In such case the amino acids can be in contact with the column resin during the activation, at least for part of the time.

When using pre-activation, the column resin may be prepared for the next building block, e.g. de-blocked, or washed during the pre-activation.

In cases when pre-activation is used, the pre-activation can be varied in terms of:

addition order of the amino acids and reagents;

type of coupling agents and optionally base and any additives;

time intervals until next component is added to the mixing chamber;

amounts of solvents, amino acids and reagents;

concentrations of amino acids and reagents;

temperature of added amino acids and reagents to the mixing chamber;

temperature during pre-activation;

time interval for pre-activation; and time interval for addition of pre-activated mixture to the column, etc.

In an example of the first aspect the column is thermally insulated.

The column may be thermally insulated during the process and/or made of material of relatively low thermal conductance (e.g. plastic, stainless steel, glass, etc.). The thermal insulation reduces the heat loss from the column allowing the amino acid mixture to keep the elevated temperature during the coupling step, allowing e.g. faster kinetics of the reaction. The column can be insulated from the outside or the inside or both. In a typical case the column comprises stainless steel and is insulated from the outside using plastic or other insulating material(s).

To further reduce the heat losses in the system, the tubings may be insulated. Also, other components of the system, such as valves, may be insulated and/or manufactured from materials that reduce heat losses, e.g. plastic or other materials of low thermal conductance.

In an example of the first aspect the volume without resin in the column is more than about 1% of the column volume.

The volume without resin in the column is at least 1% of the column volume before starting the process. A column not fully packed leaves space for the resin to swell during the process. The swelling of the resin depends on e.g. length and sequence of peptide, number of reactive sites per resin mass or resin volume (i.e. resin loading), the amino acid composition of the synthesized peptide, the combination of used solvents, etc. The process may also be run using a column that automatically changes the column volume, i.e. the resin volume is equal or close to equal of the column volume at any time during the process. The aim, when packing the column prior to synthesis start, is that the resin volume will become equal to or close to equal to the column volume during the process or at the end of the process.

The physical properties of the resin are important e.g. for the coupling efficiency and for any secondary structure formation of the growing peptide chain.

In an example of the first aspect the process is linearly scalable.

The SPPS process may be linearly scalable, i.e. the liquid flow rate in the column (in cm/h) may be the same independent of the size/proportions of the column, and hence the same linear flow rate may be used in all scales, e.g. μmol, mmol, mol etc. This means that an SPPS process according to the invention may be scaled up (or scaled down) using the same relative excess of amino acids in a smaller scale (e.g. μmol) as in a larger scale (e.g. mmol, mol), or vice versa (i.e. transfer of conditions from a larger to a smaller scale), due to the use of the same linear liquid flow rate in the various steps. Therefore, the process can be optimized in small scale prior to being upscaled or downscaled, which may save both time, reagents, solvents, and reduce waste. The process may give similar or identical results, e.g. yield and purity, in the scaled version as in the scale where the parameters were optimized. As understood by persons skilled in the art for a process to be linearly scalable not all process parameters (e.g. pressure, temperature, etc.) and not all synthesis components (e.g. additives, solvents, etc.) must have a linear relationship between different synthetic scales.

In an example of the first aspect the progress of the peptide synthesis in the column is continuously monitored using at least one detector. In further examples of the first aspect the detector is a UV/visible light detector, a near infrared (NIR) light detector, a mass spectrometry (MS) detector or a conductivity detector. In a further example of the first aspect, wherein the detector is a UV/visible light detector the light can be detected simultaneously at least at 4 different wavelengths.

The process can be continuously monitored using at least one detector, e.g. a UV/visible light detector, or an NIR light detector, or an MS detector, or a conductivity detector or a combination of several detectors. The continuously real-time monitoring provides information about the progress of the different steps: de-blocking, activation, coupling, washing, etc. Such information may for example be when the present, on-going step, is finished and the next step may begin, i.e. reaching a conditional threshold. The information from the monitoring can also be used to change the synthesis protocol depending on the output from the continuous monitoring. The process can be monitored in different ways such as for example in-line, or on-line, or both. The process may be monitored in ways that allows for continuous monitoring.

A UV/Vis detector may be used for real-time monitoring of e.g. de-blocking of e.g. Fmoc-groups, the progress of a washing cycle after e.g. de-blocking of Fmoc-groups, coupling, mixer cleaning, etc., positioning of the front or the end of e.g. the liquid stream of e.g. coupling agents, additives, bases and amino acids, etc. during transport to mixing chamber, activated amino acid mixture during addition to column, or any other addition or transport that requires detection of the position of a reagent i.e. as a liquid stream in the system. In one example the UV/Vis light can be detected e.g. at four different wavelengths simultaneously. The area under the curve and the shape of the curve can be used to predict coupling efficiency with comparison of the previous curve areas and shapes. The shape of the curve may serve as a basis for determining the coupling conditions in the next coupling step. Changes in the curve shape may indicate necessary changes in process conditions, such as coupling time, the number of repetitive couplings, reagent concentrations, reaction temperature, etc. In another example the UV/visible light detector may be used to monitor at least one range of wavelengths, i.e. taking UV/visible spectra within a light wavelength interval at different timepoints. For example, information about the composition of the liquids can be extracted from such spectra.

An NIR detector can be used to detect various components in a mixture based on specific properties identifiable from an NIR spectrum.

An MS detector can be used to detect presence of, and/or an increase or decrease of components that are expected, or unexpected, which may give information for optimization of certain steps or certain cycles or both in the process.

A conductivity detector can be used to detect e.g. salt content and can be used to measure and/or verify recirculation time and volume. This can also be accomplished by using other detectors, e.g. UV/Vis detector.

In an example of the first aspect the process uses software controlled real-time conditional monitoring and enables the use of Process Analytical Technology (PAT) to measure Critical Process Parameters (CPP) which affect Critical Quality Attributes (CQA).

The SPPS process may enable the use of Process Analytical Technology (PAT) to measure Critical Process Parameters (CPP) which affect Critical Quality Attributes (CQA). PAT is defined by the Food and Drug Administration (FDA) as a mechanism to design, analyze and control pharmaceutical manufacturing processes through the measurement of CPP that affects CQA. The enablement of PAT implies that the process is current Good Manufacturing Practice (cGMP) suitable.

The use of PAT may allow the user to choose which of the parameters e.g. time, absorbance of light at certain wavelengths, temperature, presence or absence or both of certain intermediates, by-products, etc. that control the process.

Defined parameters may be documented and logged in the control software according to 21 CFR part 11 compliance.

In one example of the first aspect the process uses software controlled real-time conditional monitoring of critical parameters, such as potential pressure increase during coupling including automated handling and subsequent decrease of pressure. An advantage with such a control is that it enables a process with longer coupling times, such as several hours, if required.

In one example of the first aspect the process is preceded by wetting and subsequent swelling and optionally equilibration of the resin packed in the column prior to combining the amino acid(s) with one or more reagents.

The process may comprise a step prior to combining the amino acid(s) with one or more reagents, wherein such a step a dry resin is wetted, subsequently swollen and equilibrated inside the column. The wetting, swelling and equilibration of the resin inside the SPPS system is performed by passing a liquid from the lower end of the column. This allows for any gas (e.g. air) to exit the column at the top prior to starting the process. Such a wetting and swelling procedure allows for adding dry resin to the column.

Equilibrated or equilibration may refer to thermal equilibration (i.e. reaching to a desired temperature), and chemical equilibration which includes washing, and/or chemical reactions, or both.

The column containing the resin and solvent can be equilibrated before the synthesis start and at certain steps during the synthesis. The equilibration may include chemical and physical equilibration, such as thermal equilibration and/or washing with solvents. For the equilibration process the column is connected to the system and a liquid flow is initiated either directly through the system including the column, or by recirculating the liquid through the tubings and the column in a closed system, or by recirculating the liquids through the column and through a mixing chamber. For thermal equilibration a temperature regulating device (e.g. heater), set at a desired temperature, is included in the flow-path before the liquid enters the column. Such an equilibration is achieved when a detector detects a parameter value (e.g. temperature, UV/VIS absorbance, conductivity, fluorescence etc.) at a predetermined interval within a predetermined time segment, i.e. a parameter has reached a stable value. This method can be used when the desired endpoint of the parameter value is not known in advance e.g. a non-conditional threshold. Alternatively, the equilibration can be achieved, when a detector detects a parameter value (e.g. temperature, UV/visible light absorbance, conductivity, fluorescence, etc.) at a predetermined level e.g. a conditional threshold. The latter method can be used when the desired endpoint of the parameter value is known in advance. For example, equilibration by recirculating the liquid through the column can be used for warming up the column to a desired temperature before the synthesis start. Equilibration by streaming a solvent through the column to waste can be used for washing the system and the column before and within a synthesis cycle. Another possibility for equilibration is that a certain predetermined volume of a liquid is passed through the system or the column. Such method can be used for e.g. capping (blocking the unreacted amino groups after a coupling step), in such case the liquid that is being passed through the system may comprise an excess of capping reagent to push the reaction towards completion.

To further improve for example the equilibration and/or reaction, the flow of liquids passing the column may be reversed once or several times during the equilibration process, i.e. redirecting the flow into the column from the upper or alternatively from the lower end.

In one example of the first aspect the process may include purge operations from or to at least one amino acid, reagent, solvent or gas inlet. The purge operations may be carried out before, during or after the synthesis. Purge operations may include e.g. delivery of a previously defined volume(s) of a liquid, e.g. amino acid solution into or from the system followed or preceded by a volume of another liquid, e.g. solvent. Purge operation may consist of a series of deliveries of several different liquids, both to and from the system. During e.g. pre-synthesis purge, a defined volume of amino acid and/or reagent solution is pumped into the system followed by a volume of solvent.

Such procedure may be carried out with one, several or all amino acid and/or reagent inlets attached to the system. However, purge operations may also consist of a procedure carried out with only one liquid delivered into or from the system, e.g. in the case of purging of solvent inlets, or e.g. backwash. Another examples of purge operations may comprise delivery of a volume of amino acid followed by a solvent to fill the tubings with fresh reagent to a certain position in the system before an activation step. A further example of purge may comprise delivery of a defined volume of solvent from the system into amino acid and/or reagent inlets to fill them with fresh solvent after the synthesis. Such procedure may be carried out during backwash of inlets.

Similar purge operations may be carried out using the gas inlets attached to the system. In an example, the gas inlets to and/or from the flasks are purged with nitrogen gas to displace air or vapors of reagents and/or solvents.

All purge procedures may be carried out in an automated manner controlled by a computer program. However, purge may also be performed manually or semi-manually, where some parts of the procedure are automated.

All the purge operations described herein are examples and are not limiting their use.

The SPPS process described herein is applicable for all types of amino acids, such as natural and non-natural amino acids, modified amino acids, functionalized amino acids, etc., included but not limited to are any changes in peptide backbone. The examples described herein are to be considered only as examples and not showing the full scope of the invention.

All examples and variants described for the first aspect can be combined with all examples and variants of the second aspect.

In a second aspect of the invention there is a system 100 for flow-through solid phase peptide synthesis (SPPS), wherein the system comprises at least one column 101 packed with resin, at least one pump 102, reservoirs for amino acids and reagents 104, at least one temperature regulating device 103, at least one temperature sensor 105, at least one detector 106 and at least one gas (bubble) detector 107, wherein tubing 108 connects the reservoirs 104 to the column 101. Such an SPPS system is schematically illustrated in FIG. 1. The system 100 further comprises a process 300 in communicative communication with the system 100.

The system 100 can further comprise valves 109*a-e* and/or flow re-directing valves 120*a-c* arranged to direct the flow in the system 100. The valves 109*a-e* and/or flow re-directing are in communicative communication with the processor 300.

The system 100 may be arranged to provide a re-circulation loop for peptide synthesis. In a re-circulation loop the synthesis liquid, i.e. the amino acid(s), the reagent(s), the solvent(s), and the additive(s) are re-circulated at least once over the column 101. In such case the synthesis liquid pass over the column 101 and through at least part of the tubings 108 of the system 100 at least twice.

A temperature regulating device 103 can be arranged to either heat or cool, or both, a liquid, a liquid mixture or a synthesis liquid mixture etc. in the system 100.

Figure 2:
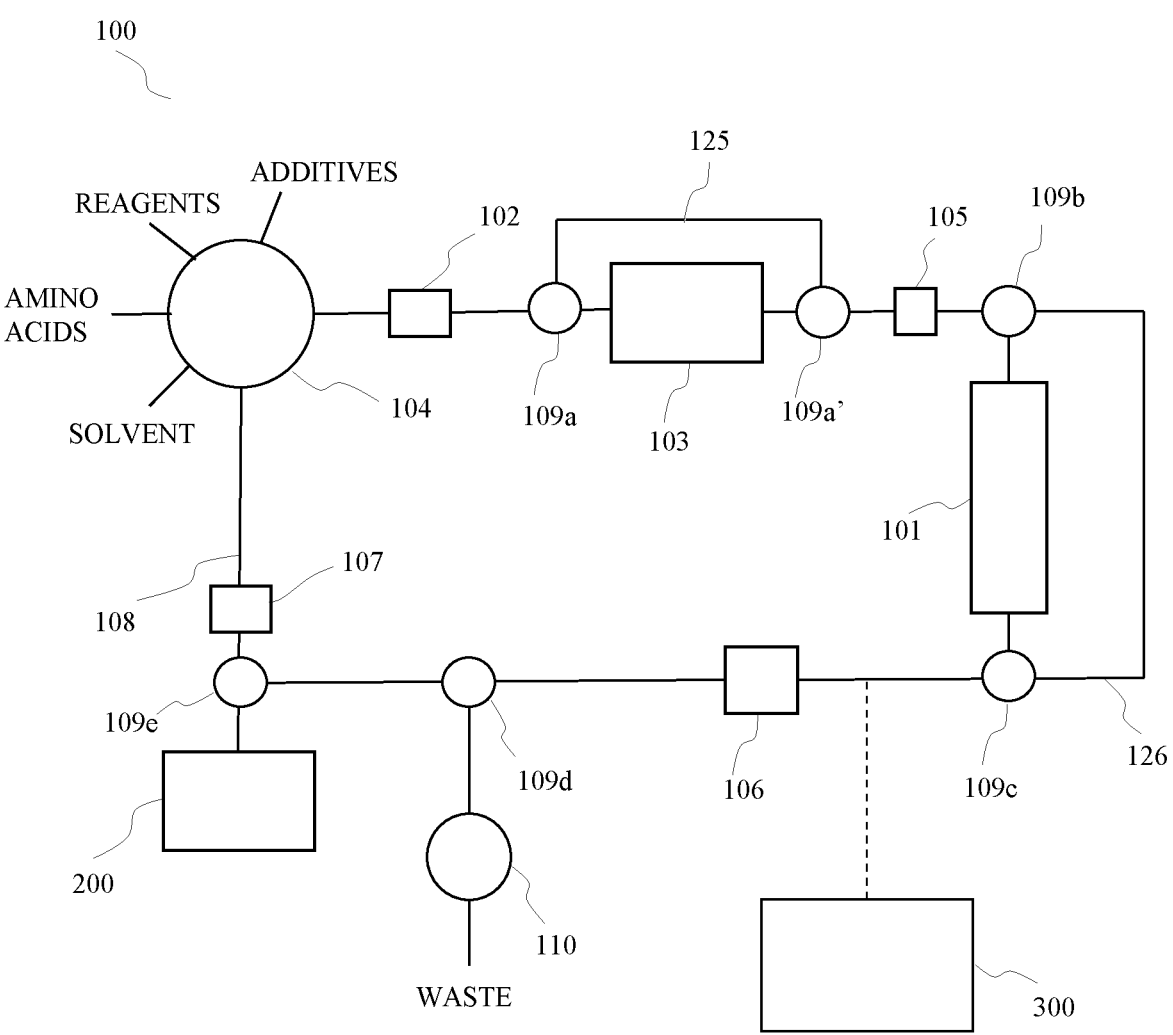
FIG. 2. is a schematic illustration of one example of a system according to the invention.

In one example of the second aspect, there is an SPPS system, FIG. 2, comprising at least one column 101 packed with resin, at least one pump 102, at least one temperature regulating device 103, reservoirs for amino acids, reagents, solvent(s) and additives 104, at least one temperature sensor 105, at least one detector 106, and at least one gas bubble detector 107, wherein tubings 108 connects the reservoirs 104 to the column 101 and valves 109*a-e* are arranged to direct the flow. The SPPS system 100, may additionally comprise a reservoir for waste 110, a temperature-regulating device bypass 125, and a column bypass 126. The system 100 further comprises a processor 300 in communicative communication with the system 100. The system 100 may further comprise a separately defined mixing chamber 200, as illustrated in FIG. 2. The processor 300 is in communicative connection with at least the valves 109*a-e*, the pump 102, the temperature sensor 105, the detector 106, the gas bubble detector 107, and the temperature regulating device 103.

In one example of the second aspect, there is an SPPS system comprising at least one column 101 packed with resin, at least one pump 102, at least one temperature regulating device 103, reservoirs for amino acids, reagents, solvent(s) and additives 104, at least one temperature sensor 105, at least one detector 106, and at least one gas bubble detector 107, a reservoir for waste 110, wherein tubings 108 connects the reservoirs 104 to the column 101 and valves 109*a-e* are arranged to direct the flow. The SPPS system may additionally comprise flow redirecting valves 120*a-c*, at least one pressure sensor 121, at least one back pressure regulator 122, at least one in-line filter 123, at least one inlet filter 124, at least one temperature regulating device bypass 125, at least one column bypass 126, a second temperature sensor 105', at least one temperature-regulating device bypass 125. The system 100 comprises a processor 300 and may further comprise a separately defined mixing chamber 200. FIGS. 3 and b shows illustrations of different configurations of a system 100 according to the example described above. The processor 300 is in communicative connection with at least the valves 109*a-e*, the flow re-directing valves 120*a-c*, the pump 102, the temperature sensor 105, the detector 106, the gas bubble detector 107, and the temperature regulating device 103. The system 100 is arranged to perform flow-through peptide synthesis, or re-circulation peptide synthesis wherein the amino acids are re-circulated over the column 101 at least once. The coupling of an amino acid to an immobilized handle, amino acid or peptide is arranged to occur in the column 101 during use of the system 100. The column 101 is packed with resin at which the peptides are immobilized during use of the system 100. A typical flow-through solid phase peptide synthesis, or re-circulation peptide synthesis, starts by arranging, e.g. opening, the first valve 109*a* arranged downstream the reservoir 104, it can also be several reservoirs. By opening the first valve 109*a* arranged downstream the reservoir 104 amino acids or peptides, optionally additives, optionally reagents, and optionally solvents can flow into the system 100 during use of the system 100. During the first step of a flow-through peptide synthesis, or re-circulation peptide synthesis, the amino acids or peptides are combined with one or more reagents. The combination, or mixing, occurs either in a separately defined mixing chamber 200 or in the tubing 108 of the system 100 (in-line mixing), or directly in the column 101 during use of the system 100.

In all examples of the second aspect the first step may be preceded by a washing step wherein the resin arranged in the column 101 is washed with a solvent or a mixture of solvents and possible co-solvents, for example in order to provide a resin ready for the first synthesis cycle. In such case the system 100 is arranged to provide a solvent to the column 101 from the reservoir 104 by opening at least the first 109a and the second valve 109b.

Figure 3A:
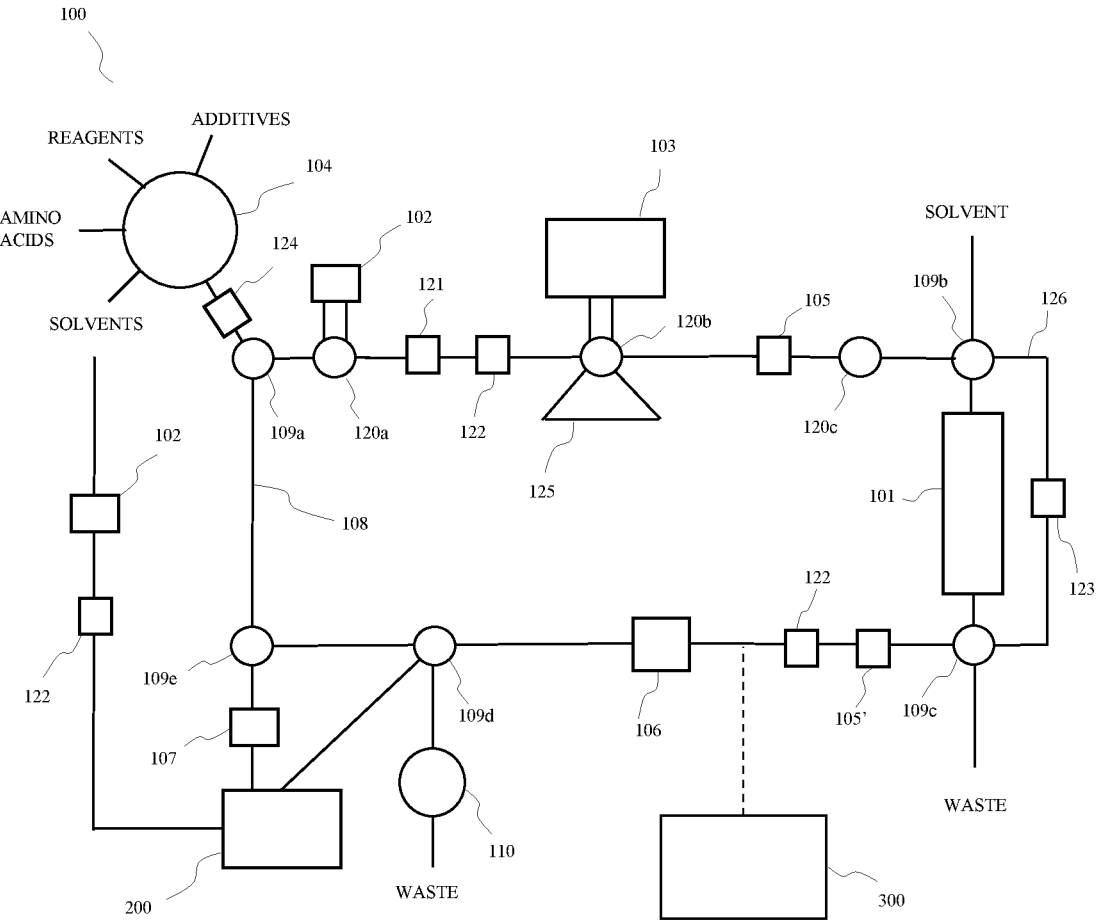
FIG. 3 *a* and *b* are schematic illustrations of examples of systems according to the invention.
Figure 3B:
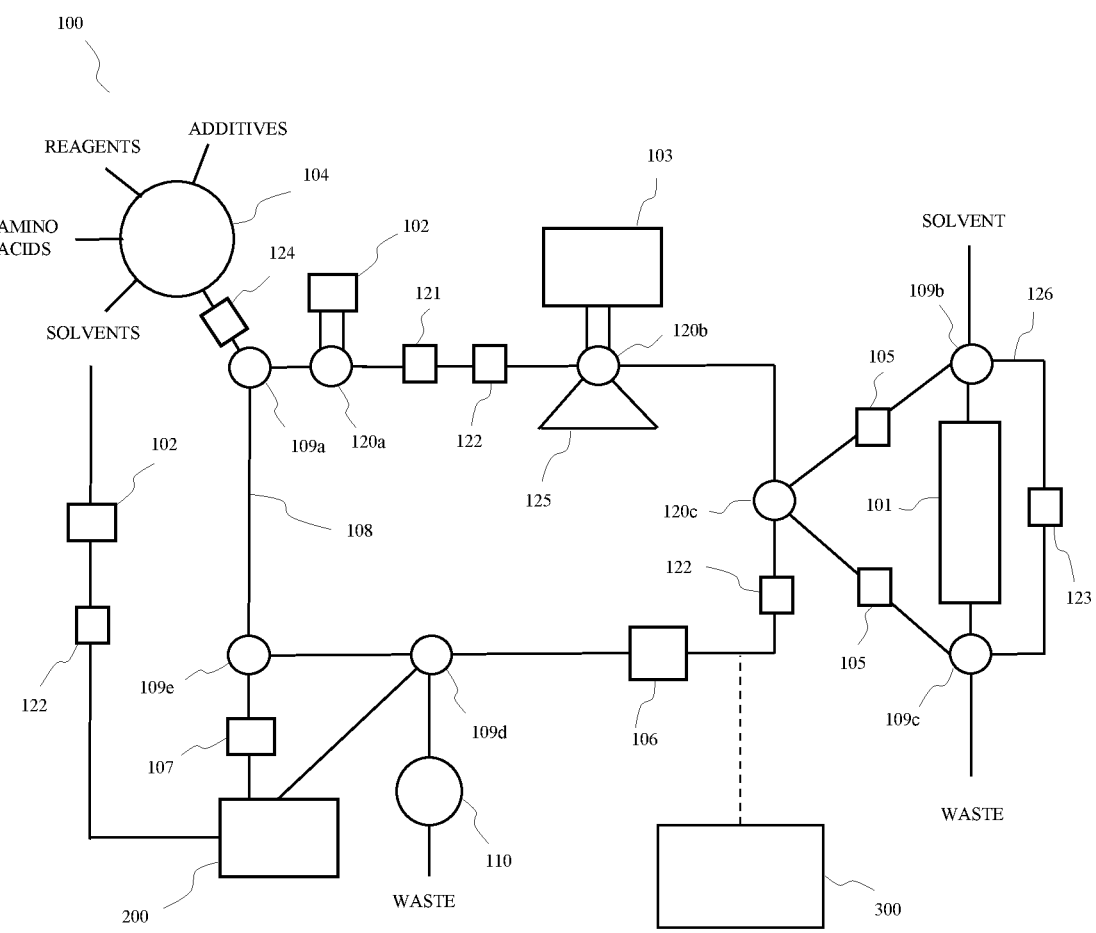

In an example of the second aspect the system 100 further comprises a separately defined mixing chamber 200. The separately defined mixing chamber 200 is arranged downstream the reservoir 104, or several reservoirs. At least one valve, e.g. the fourth valve 109d is arranged prior to the separately defined mixing chamber 200, the fourth 109d and/or the fifth 109e valve is arranged to control the flow in and out from the separately defined mixing chamber 200. If the mixing occurs in the tubing 108 of the system 100 the column bypass 126 may be arranged to allow the components of the synthesis liquid to be mixed prior to flow over the column 101. In such case the flow of amino acids or peptides, optionally additives, optionally reagents, and optionally solvents can be directed into the column bypass 126 by a third flow redirecting valve 120c arranged downstream the reservoir 104 and upstream the column bypass 126, as illustrated in FIG. 3b. Hence, the third flow redirecting valve 120c may be arranged to direct the flow into the column bypass 126. In another example, as illustrated in FIG. 3a, the second valve 109b can be arranged to control the flow into the column bypass 126.

In one example of the second aspect the temperature regulating device 103 is arranged to heat the amino acids or peptides, optionally additives, optionally reagents in the system 100. The temperature regulating device 103 is arranged downstream the reservoir 104 and upstream the column 101, hence the amino acids are heated prior to reaching the column 101 during use of the system 100. The system 100 may comprise a temperature regulating device bypass 125 arranged in connection with the temperature regulating device 103. The temperature regulating device bypass 125 may be arranged to bypass the synthesis liquid from the temperature regulating device 103, so that it does not pass the temperature regulating device 103.

In the second step of a flow-through peptide synthesis, or re-circulation synthesis, the amino acids, or peptides, are activated in the system 100. The separately defined mixing chamber 200 can be arranged to activate the amino acids, or peptides, the separately defined mixing chamber 200 is arranged as described above. The tubing 108 and/or the column 101 can be arranged to activate the amino acids, or peptides. Activation in the tubing 108 can be referred to as in-line activation. During the activation additives can optionally be added to the system 100 by opening the first valve 109a arranged downstream the reservoir 104, or several reservoirs.

In a third step of a flow-through peptide synthesis the activated amino acids, or peptides, are arranged to pass over the column 101. Inside the column 101 the activated amino acids, or peptides, are coupled to an immobilized handle, amino acid or peptide during use of the system 100. The activated amino acids, or peptides, pass over the column 101 either from the top down or from the bottom up, or both interchangeably, during use of the system 100. The second 109b and the third valve 109c that are arranged at either end of the column 101 are arranged to control the flow into as well as out from the column 101.

In a fourth step of a flow-through peptide synthesis, or re-circulation synthesis, any unreacted fraction of e.g. the N-terminal amino group(s) on the growing peptide are capped, during use of the system 100, to block these from unwanted reactions. In order to cap N-terminal groups, and possible other groups, a capping solution is arranged to pass over the column 101 by first opening the first valve 109a arranged downstream the reservoir 104, or several reservoirs, comprising the capping solution. After opening of the first valve 109a the capping solution can pass downstream the system 100 through the tubing 108 until it reaches the column 101 where it passes at least once over the column 101, during use of the system 100.

In a fifth step of a flow-through peptide synthesis, or re-circulation synthesis, the system 100 is arranged to pass a solvent over the column 101 by first opening the first valve 109a arranged downstream the reservoir 104, or several reservoirs, to allow solvent or a mixture of solvents to flow downstream the system 100 and pass over the column 101. The solvent washes out any excess amino acids, reagents and soluble by-products, hence wash out waste, from any of the previous steps e.g. de-blocking, coupling, capping etc. during use of the system 100. The system 100 is arranged to remove the waste at either of the waste outlets that may comprise a reservoir for waste 110, e.g. via the fourth valve 109d arranged upstream the reservoir for waste 110. The waste outlets are arranged downstream the column 101 and the directing of the flow to either waste outlet is controlled by the third 109c or fourth 109d valve, as illustrated in FIGS. 3a and 3b. The washing can be monitored by the detector 106, the detector 106 may be a UV/VIS monitor/detector or any other suitable kind of detector. The detector 106 is arranged downstream the column 101 and in communicative communication with the processor 300.

While a single reservoir 104 is illustrated in FIGS. 1-3 it should be understood that multiple reservoirs, e.g. each containing different types of solvents, amino acids, different reagents etc., could be used instead of a single reservoir 104. It should further be understood that the different components of the system 100 such as the detector 106, the gas bubble detector 107, the pump 102, the temperature device 103, in-line filters 123; 124, back-pressure regulator 122 etc., could be arranged at different positions in the SPPS system 100. It should be noted that the FIGS. 1-3 merely show a few examples of possible configurations of the components in the SPPS system 100.

The respective valves 109a-e are arranged to be automated and controlled by the processor 300 in order to either add solvent(s), amino acids, etc., or to remove waste, etc. They may be regulated depending on the feedback to the system 100 from the monitoring. Such regulation is provided by the processor 300 in e.g. a computer that is in communicative connection with the SPPS system 100, FIGS. 2 and 3a and b. The presence of the processor 300 in the system 100 enables an automatic process wherein the process is controlled by UV (or other detector, e.g. fluorescence) analysis, or the gas bubble detector 107, or another detector, or a combination of detectors. In other words, the processor 300 is arranged to enable the use of PAT.

The resin is arranged as a packed bed in the column 101, hence the column 101 represents a packed bed column. Any type of resin may be used to immobilize the peptides, such as, but not limited to, microporous resin, mesoporous resin, macroporous resin, e.g polystyrene based, gel-type resins, polyethylene glycol (PEG) based, polyacrylate, polyacrylamine resin or combinations thereof, etc. In a flow-through SPPS system 100 there is a reduced risk for mechanical breakdown of the resin, as compared to batch processes, since e.g. no stirring is applied.

The temperature regulating device 103 can be e.g. an electric heating device, a water bath, or an oil bath, or an induction heater, or a microwave cavity, etc. The temperature regulating device 103 is arranged upstream the column 101 to allow heating of the amino acid mixtures prior to being added to the column 101.

In an example of the second aspect the system comprises at least two columns or more, such as 10 columns.

The SPPS system 100 may comprise more than one column 101, e.g. at least two columns 101 that can be connected in parallel. The use of more than one column 101 facilitates automated sequential synthesis of other sequences, synthesis in different scales, optimization of parameters for process development, etc.

In an example of the second aspect the system 100 further comprises a detector 106 selected from a UV/visible/diode array detector, a fluorescence detector, an NIR detector, a mass spectrometry detector and a conductivity detector. Several different detectors may be connected sequentially or in parallel. The detector 106, or several detectors, are in communicative connection with the processor 300.

In another example of the second aspect the column 101 is thermally insulated.

In another example of the second aspect the system 100 further comprises a separately defined mixing chamber 200.

The SPPS system 100 may comprise at least one separately defined mixing chamber 200. The separately defined mixing chamber 200 can be arranged to e.g. activate the amino acids, interim storage of compounds and/or solutions, or solvents etc. When the separately defined mixing chamber 200 is used to activate the amino acids, the resin may be de-blocked and/or washed during the activation step. The gas bubble detector 107 can be arranged to monitor when the mixing chamber 200 is emptied and the activated amino acids have entered the tubing 108 of the system, i.e. the gas bubble detector 107 is arranged to detect when the mixing chamber 200 is empty. The gas bubble detector 107 is in communicative communication with the processor 300. The gas bubble detector 107 can also be arranged to be used during the washing procedure of the mixing chamber 200 to monitor when the mixing chamber 200 is empty, i.e. using a conditional threshold. The gas bubble detector 107 may also be arranged in any other place in the system 100 to monitor gas bubbles, e.g. for detecting emptying of reagent and solvent reservoirs 104. As apricated by the skilled person, also other types of sensors and detectors can be used for monitoring of the emptying of the mixing chamber 200 and/or reservoirs 104, such as, but not limited to capacitance, ultrasonic, microwave, and optical sensors and detectors.

In one example of the second aspect the volume without resin in the column 101 is more than about 1%.

Having a column 101 that has a volume without resin of at least 1% allows for wetting and swelling of the resin prior to or during the process.

In one example of the second aspect the system 100 comprises a protective gas in at least one reservoir 104.

The system 100 may comprise one or several gas manifolds (not shown), wherein gas is arranged to be distributed to one, several, or all reservoirs 104 including the separately defined mixing chamber 200. The type of the gas is preferably an inert gas such as nitrogen or argon, but also other gases or gas mixtures may be used. The gas may function as a protective gas in one or several of the reservoirs 104, i.e. by pressurizing the reservoir 104. The gas may also facilitate transfer of building blocks, reagents solvents, etc. from the reservoirs 104 to the rest of the SPPS system 100. The gas pressure may for example be 0.01 bar to 1.0 bar or higher. The gas pressure depends on the components in the SPPS system 100 and can be determined by a person skilled in the art.

In one example of the second aspect the SPPS system 100 further comprise at least one inlet filter 124. The inlet filter 124 may be arranged to prevent particle(s) from entering into the SPPS system 100. Any particles that enter the SPPS system 100 may disturb or (partly) destroy parts of the SPPS system 100, e.g. valves 109a-e, pump(s) 102, detector(s) 106 etc. Particles that enter the SPPS system 100 may also interfere with the chemical reactions and the monitoring of the process. An inlet filter 124 may for example be arranged at the tip of one or several inlet tubings, such as at the tip of each inlet tubing, e.g. downstream the reservoir(s) 104 and upstream the first valve 109a, or upstream of the pump 102. An inlet filter 124 can for example comprise porous polyethylene, polypropylene, glass or any other suitable material. A suitable pore size of the inlet filter 124 depends on the process and the SPPS system 100 and can be determined by a person skilled in the art.

In one example of the second aspect of the system the SPPS system 100 further comprises at least one in-line filter 123. An in-line filter 123 may be arranged to filter off unwanted components such as e.g. precipitates that have formed during the process. An in-line filter 123 can for example be placed upstream or downstream the pump 102 or at any other suitable position in the SPPS system 100.

In one example of the second aspect the SPPS system further comprises at least one flow redirecting valve 120a-c. A flow redirecting valve 120a-c can be arranged to reverse the flow in the SPPS system 100, either in the entire system 100 or in selected parts. The flow may for example be reversed during filling of the column 101 with liquid prior to starting the synthesis, during coupling of amino acids to compensate for a possible temperature gradient, for cleaning purposes, etc. A first flow redirecting valve 120a can be arranged in connection with the pump 102. A second flow redirecting valve 120b may arranged in connection with the temperature-regulating device 103 and the temperature regulating device bypass 125. The processor 300 is in communicative connection with the at least one flow redirecting valve 120a-c.

In one example of the second aspect the at least one flow re-directing valve 120a-c comprises at least two positions. For example one position is arranged so that the flow enters the column 101 or column bypass 126 in a clockwise, and the second position arranged so that flow is reversed, i.e. counterclockwise.

A third flow redirecting valve 120c may be arranged so that it is connected to the column 101, or columns in the case of several columns in the SPPS system 100.

The flow redirecting valve 120a-c may further be integrated into the valves 109a-e, for example the second 109b and third 109c valves that connects the column 101 to the rest of the SPPS system 100, or at any other suitable position in the SPPS system 100. By placing a first flow redirecting valve 120a connected to the pump 102 the first flow directing valve 120a may be arranged to change the flow direction of the synthesis liquid in the system 100. A second flow redirecting valve 120b arranged in connection with the temperature regulating device 103 may be arranged to switch the flow between the temperature regulating device bypass 125 and the temperature regulating device 103.

In one example of the second aspect the SPPS system 100 further comprises at least one back-pressure regulator 122. A back-pressure regulator 122 may be arranged to increase the back pressure in the SPPS system 100 which may improve compression of air bubbles in the SPPS system 100, the performance and/or function of the valves 109a-e, pump(s) 102, detector(s) 106, column(s) 101, etc. Regulation of back pressure may be beneficial in terms of allowing inert gas pressure in the reservoir(s) 104 and mixing chamber(s) 200. The back pressure may be set to for example 0.1 bars, 1 bar, 2 bars, 3 bars, 10 bars, 20 bars, etc. The back pressure value depends on the components in the SPPS system 100.

In one example of the second aspect the SPPS system 100 further comprises at least one column bypass 126. The column bypass 126 may be arranged to recirculate liquids in the SPPS system 100 without passing the column 101, for example during pre-activation of amino acids, during washing of the SPPS system 100, etc.

In one example of the second aspect the SPPS system 100 further comprises a temperature regulating device bypass 125, such a temperature regulating device bypass 125 may for example be a liquid channel. The temperature regulating device bypass 125 may be arranged to allow the liquid flow to bypass the temperature regulating device 103, as discussed above.

In one example of the second aspect the pressure inside the SPPS system 100 is regulated by adjusting liquid flowrate or by adjusting back-pressure regulator 122 or both in combination.

The pressure inside the column 101 during use of the system 100, measured by at least one pressure sensor 121 in the SPPS system 100, may vary during the process due to, for example, different flow rates, expansion of the resin by growing peptide, use of certain solvents, size of the equipment components such as tubing, etc. The pressure sensor 121 may be arranged downstream the pump 102 and upstream the column 101. At least one pressure sensor 121 may be arranged to continuously monitor the pressure inside the SPPS system 100. The liquid flowrate is arranged to be adjusted based on the pressure so that the pressure inside the SPPS system 100 is kept within predetermined limits, during use of the system 100. Such predetermined limits depend on the process and the components of the SPPS system 100 and is to be determined by a person skilled in the art.

In one example of the second aspect, schematically illustrated in FIG. 3a, the first valve 109a is arranged downstream and in fluid communication with the reservoir(s) 104, and in fluid communication with the first flow re-directing valve 120a arranged downstream the first valve 109a. The first flow re-directing valve 120a is in fluid communication with the pump 102, the second flow re-directing valve 120b is arranged downstream and in fluid communication the first flow re-directing valve 120a. The second flow re-directing valve 120b is in fluid communication with the temperature regulating device 103 and with the temperature regulating device bypass 125. The temperature sensor 105 is arranged downstream and in fluid communication with the second flow re-directing valve 120b. The third flow re-directing valve 120c is arranged downstream and in fluid communication with the temperature sensor 105. The second valve 109b is arranged downstream and in fluid communication with the third flow re-directing valve 120c, and upstream and in fluid communication with the column bypass 126 and the column 101. The column 101 is arranged upstream and in fluid communication with the third valve 109c, that is arranged downstream and in fluid communication with the column bypass 126. The third valve 109c is arranged downstream and in fluid communication with the detector 106, that is arranged downstream the fourth valve 109d. The fourth valve 109d is arranged in fluid communication with the waste outlet 110 and with the separately defined mixing chamber 200, and downstream and in fluid communication with the fifth valve 109e. The fifth valve 109e is arranged in fluid communication with the separately defined mixing chamber 200. The gas bubble detector 107 is arranged upstream and in fluid communication with the separately defined mixing chamber 200, and downstream the fifth valve 109e. The fifth valve 109e is arranged downstream and in fluid communication with the first valve 109a. The tubings 108 connects the valves 109a-e with the flow re-directing valves 120a-c, the reservoir(s) 104, the column 101, the temperature regulating device 103, the pump 102, the temperature sensor 105, the detector 106, the gas bubble detector 107, the waste outlet 110, and the separately defined mixing chamber 200. The processor 300 is in communicative communication with at least the valves 109a-e, the flow re-directing valves 120a-c, the temperature regulating device 103, the pump 102, the temperature sensor 105, the detector 106, and the gas bubble detector 107.

In one example of the second aspect the flow out from the separately defined mixing chamber is via the gas bubble detector 107 and the fifth valve 109e, and the flow into the separately defined mixing chamber 200 is via the fourth valve 109d. The tubing 108 that connects the separately defined mixing chamber 200 with the fifth valve 109e, i.e. the tubing for the outflow, is arranged in the bottom of the separately defined mixing chamber 200.

The system 100 is arranged to perform flow-through, or re-circulation, peptide synthesis. Such a synthesis can be described in the following method 400, FIG. 4:

Step 401: In a first step of the synthesis the processor 300 controls the first valve 109a so that the first valve 109a is opened. Once the first valve 109a is opened amino acids or peptides, optionally additives, reagents, and solvents, i.e. the synthesis liquid, flow from the reservoir 104 into the system 100. The pump 102 is arranged to control the flow inside the system 100. In one example the synthesis liquid passes an inlet filter 124 on its way from the reservoir to the tubing 108 of the system 100. The synthesis liquid is mixed by flowing it through the system 100 in the tubing 108, without passing the column 101 or the temperature-regulating device 103, i.e. in step 401 the synthesis liquid flows through the temperature regulating device bypass 125 and the column bypass 126. This is controlled by the processor 300 by controlling the flow-redirecting valves 120a; 120b; 120c and the second 109b and third valve 109c.

In one example the mixing of the synthesis liquid is arranged to occur in the separately defined mixing chamber 200 during use of the system 100. In such case the synthesis liquid flow from the reservoir 104 to the separately controlled mixing chamber 200 without passing the column 101 or the temperature-regulating device 103, in the same way as described above. The synthesis liquid enters the separately defined mixing chamber 200 via the fifth valve 109e that are in communication with and controlled by the processor 300.

In one example the mixing of the synthesis liquid is arranged to occur in the column 101. In such case the synthesis liquid flow from the reservoir 104 to the column 101 via the temperature-regulating device 103, or, bypassing the temperature regulating device 125 (optional) and optionally bypassing the column via the column bypass 126 at least once prior to addition to the column 101. The flow of synthesis liquid enters the temperature regulating device 103 via the second flow-redirecting valve 120b and via the first valve 109a that both are in communication with and controlled by the processor 300.

Step 402: In a second step of the synthesis the amino acids, or peptides, are activated inside the system 100. In one example the amino acid(s) or peptides are activated in the separately defined mixing chamber 200. In such case the amino acid(s) and optionally activation additives flow from the reservoir 104 to the separately defined mixing chamber 200, during use of the system 100, by controlling at least the first valve 109a, and the fifth valve 109e with the processor 300. Depending on configuration of the system 100 additional valves 109a; 109b; 109c; 109d and/or flow re-directing valves 120a; 120b; 120c may be controlled as well.

In one example the amino acids, or peptides, are activated in the tubing 108 by flowing the synthesis liquid through the tubing 108. The liquid is arranged to flow through the system 100 during use by controlling at least the first valve 109a, and the fifth valve 109e by the processor 300. Depending on the system 100 additional valves 109a; 109b; 109c; 109d and/or flow re-directing valves 120a; 120b; 120c may be controlled as well.

During step 402 additives may be added from the reservoir 104 to the synthesis liquid via the first valve 109a that is communication with and controlled by the processor 300.

The detector 106 is arranged to monitor the activation step 402, the detector 106 is in communicative communication with the processor 300.

In one example step 402 is followed by a step 402' wherein the separately defined mixing chamber 200 is emptied. The detector 106 and/or the gas bubble detector 107 may be arranged to monitor the emptying of the separately defined mixing chamber 200. In step 402' the separately defined mixing chamber 200 is emptied by flowing liquid from the separately defined mixing chamber 200 to the column 101. The system 100 is arranged to direct the flow by arranging at least the fifth 109e, the first 109a, and the second valve 109b. The system 100 is further arranged to direct the flow from the column 101 to the waste reservoir 110 by arranging at least the third valve 109c and the fourth valve 109d. The gas bubble detector 107 and the detector 106 are arranged to monitor the step 402' of emptying the separately defined mixing chamber 200. When indicated by at least one the gas bubble detector 107 or the detector 106 the system 100 is arranged to flow the liquid from the fourth valve 109d back to the separately defined mixing chamber 200 or to the waste container 110.

Step 403: In a third step of the synthesis the activated amino acids are arranged to pass over column 101 in order to form a peptide, i.e. the coupling step. During use of the system 100 the activated amino acids are inside the tubing 108 and are arranged to flow through the tubing 108 by control of the pump 102 which is in communication with and controlled by the processor 300. In one example the synthesis liquid comprising activated amino acids are arranged to pass over the column from the top by arranging (e.g. opening) the second valve 109b via the processor 300. In one example the synthesis liquid comprising activated amino acids are arranged to pass over the column from the bottom by arranging the third valve 109c via the processor 300.

Figure 4:
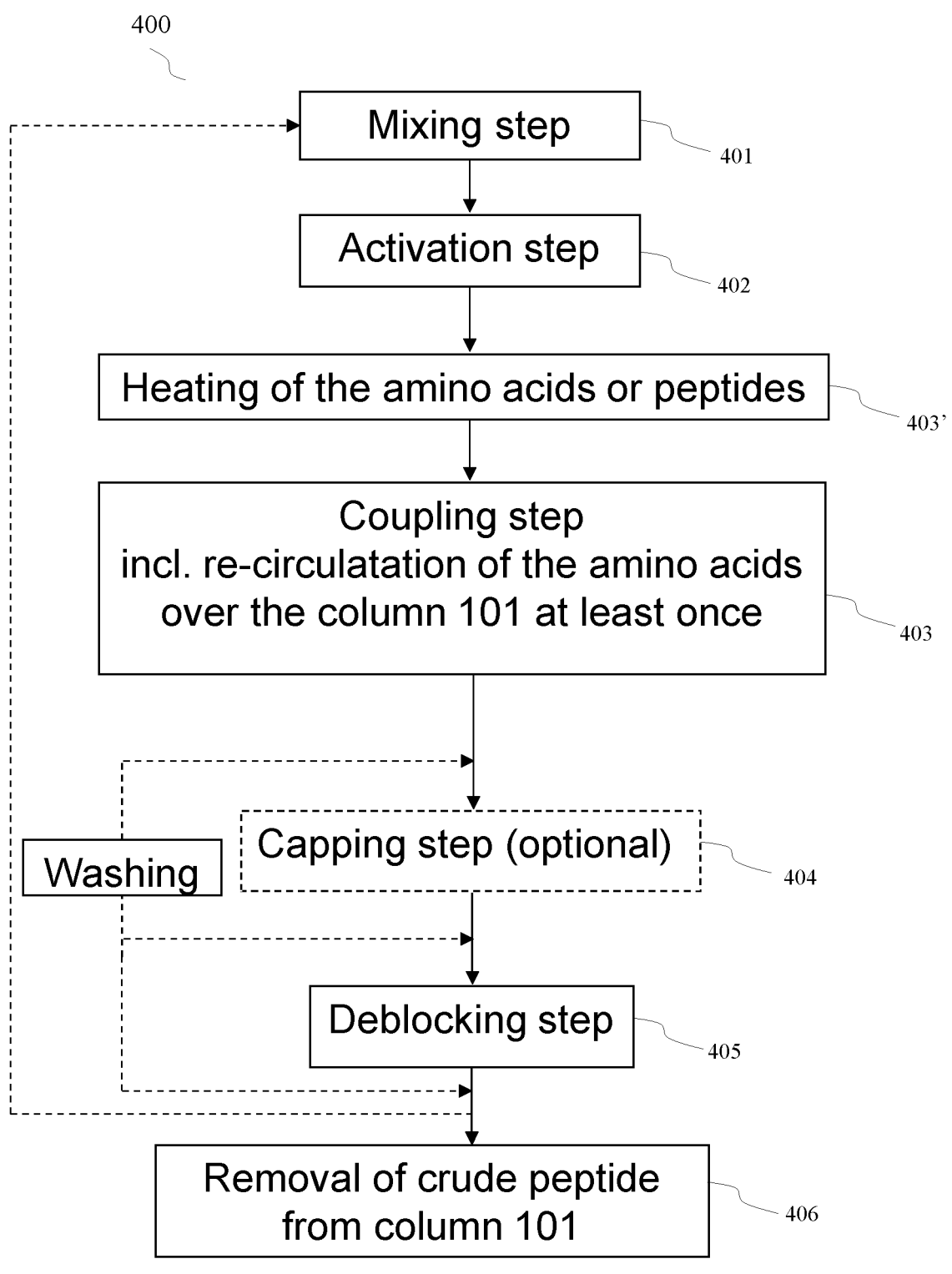
FIG. 4 is a flow-chart of one example of the invention.

In all aspects of the invention the synthesis liquid comprising the activated amino acids is arranged to pass the temperature regulating device 103 prior to entering the column 101, as illustrated in FIG. 3b and FIG. 4 (step 403'). The temperature regulating device 103 is arranged to heat and/or cool the amino acids. The system 100 is arranged to pass the activated amino acids through the temperature regulating device 103 by arranging at least one of the first valve 109a, the first 120a and second 120b flow redirection valves.

In all aspects of the invention the synthesis liquid comprising activated amino acids are re-circulated over the column 101 at least once. Hence, the processor 300 is arranged to control the pump 102, the valves 109a-e and the flow re-directing valves 120a-c so that the synthesis liquid flow through the system 100 in the tubing 108 and over the column 101 at least twice.

Step 404 Capping step (optional). In a fourth step of the synthesis, after the coupling step 403 any unreacted fraction of the terminal groups, i.e. the N-terminal groups can be capped. In step 404 the system 100 is arranged to provide a capping solution to the column 101. The processor 300 is arranged to control the first valve 109a so that a capping solution enters the tubing 108. The pump 102 is arranged to control the flow of the capping solution so that it is passed over the column 101 at least once. The processor 300 is arranged to control at least the first valve 109a and the second valve 109b, optionally also the first second valve 109a' (see FIG. 2), the first 120a and second 120b flow redirecting valve so that step 404 can be carried out.

In one example the system 100 is arranged to perform a washing step after any of the steps 402, 402', 403, 404, 405 described above. In the washing step at least one solvent is passed over the column 101. The processor 300 is arranged to control the first valve 109a so that solvent flow downstream the system 100 and pass the column 101. The processor 300 is further arranged to control following the first 109a, second 109b, and third 109c valves and flow redirecting valves 120a-c so that the solvent can flow through the system 100 and over the column 101. After being passed over the column 101 the solvent comprises waste is arranged to be removed from the system 100. The solvent comprising waste exits the column 101 via the third valve 109c that is in communication with and controlled by the processor 300. In one example a waste outlet is directly connected the third valve 109c, see FIGS. 3a and b, and the waste solvent is arranged to exist the system 100 there. In one example the waste solvent is arranged to exit the system 100 via the reservoir for waste 110 via the fourth valve 109d that is in communication with and controlled by the processor 300. The detector 106 is arranged to monitor the washing and controlled by and in communication with the processor 300.

Step 405 De-blocking step. In a first or fifth step of the synthesis (depending on need of de-blocking prior to first coupling), the protected e.g. Fmoc, N-terminal groups are de-blocked so that the protecting groups are removed. In the deblocking step 405 the system 100 is arranged to provide a de-blocking solution to the column 101, in the same way that is described in step 404.

After the capping step 405, the system 100 is arranged to repeat steps 401-404 or steps 401-405 until the desired peptide is formed.

Step 406 Removal of the crude peptide. In the last step of the reaction the crude peptide is cleaved off from the resin arranged either in the column 101 or outside the column 101.

During the different steps the liquid may pass at least one in-line filter 122.

The flow of liquid in the system 100 is arranged to be controlled by the pump 102 that is in communicative communication with and controlled by the processor 300.

The system 100 are arranged to control the peptide synthesis via the detector 106 that is in communication with the processor 300.

In all steps of the method 400 the pump 102 is arranged via the processor 300 to control the flow of liquid in the system 100. The pump 102 is in communicative communication with the processor 300.

In one example of the second aspect it is possible to reverse the flow in the system 100 using one or several of the flow re-directing valves 120*a*; 120*b*; 120*c*.

All examples and variants described for the second aspect can be combined with all variants and examples of the first aspect.

EXAMPLES

Example 1

Synthesized peptide. For evaluation of the synthesis performance of the instrument an analogue of Bivalirudin having the amino acid sequence FPRPGGGGNGDFEE-IPEEYL-amide was used, where each letter denotes a one-letter code for amino acids.

Preparation and attachment of reagents to the system. Containers containing solutions made up in N,N-dimethylformamide (DMF) of Fmoc-amino acids (0.5 M), coupling reagent (0.5 M N,N'-diisopropylcarbodiimide, DIC), and additive (0.5 M ethyl cyano(hydroxyimino)acetate, Oxyma-Pure, or 0.5 M hydroxybenzotriazole, HOBt) were connected to the synthesizer. DMF was connected to the system. 20% piperidine (v/v) and 10% acetic anhydride (v/v), both prepared in DMF, were connected to their predetermined inlets. All inlets were purged to eliminate gas (e.g. air) from the tubings and to fill the tubings with the corresponding solutions or solvents.

Heater (i.e. temperature regulating device). The temperature of the heater was adjusted to achieve 43° C. in the column. The pre-activation step was carried out at ambient temperature by-passing the heater. Fmoc-amino acid coupling and Fmoc-group de-blocking steps were carried out using solutions passing through the heater.

Preparation of the column reactor. Fmoc-Rink amide resin (2.777 g, loading 0.41 mmol/g, polystyrene crosslinked with 1% divinylbenzene) was loaded to the column reactor, the column reactor was connected to the instrument. The resin was wetted and subsequently swelled using DMF by pumping the liquid into the column from bottom up. Contrary to resin swelling, synthesis steps were performed by passing the liquids from the top down through the column. However, the liquids/solutions/solvents can alternatively be passed through the column from bottom up during any part of the process.

Synthesis using pre-activation in a separately defined mixing chamber and coupling of activated amino acids. Two equivalents of 0.5 M Fmoc-amino acid solution (4.55 ml) was pumped from the amino acid container into the mixer at flow rate 9.1 ml/min, followed by 2 equivalents of 0.5 M OxymaPure solution (4.55 ml at 9.1 ml/min) and 6 equivalents of 0.5 M DIC solution (13.66 ml at 20 ml/min). The reagents were mixed in the mixing chamber by recirculation, by-passing both the column and the heater, at a flowrate of 30 ml/min for 5 min at room temperature. Then the activated amino acid was pumped from the mixer into the column at 100 cm/h through the heater. The pumping was monitored by UV- and gas bubble detectors. The mixture was then recirculated for a pre-determined time at flowrate 200 cm/h, directly followed by capping.

Synthesis using in-line activation and coupling of activated amino acids. The same amounts of Fmoc-amino acid, additive and coupling reagent as indicated above were pumped directly into the column reactor through the column heater. Re-circulation of the mixture was performed at 200 cm/h and continued for a predetermined time, followed by capping.

Capping. The amino acid coupling step was followed by capping using 10% acetic anhydride in DMF (v/v) (30 equivalents at 150 cm/h). The column reactor was then washed with DMF at 200 cm/h. The progress of the washing was monitored and controlled by UV detection.

Fmoc-group removal. The column reactor was treated with 20% piperidine in DMF (v/v) to remove the Fmoc protecting groups. The UV absorbance peak was monitored, and the peak area, height and width at half-maximum were calculated and plotted for each Fmoc removal step during each cycle. At a predetermined level of UV absorbance during the Fmoc peak removal (at 20% of the eluted peak height) the eluent was changed to DMF for washing. The column was then washed with DMF before starting the next synthesis cycle, i.e. coupling of the next amino acid.

Mixer washing. The mixer was washed using DMF. Cleanliness of the mixer was monitored by UV absorbance. The emptying of the mixer was monitored using the air bubble detection. After mixer washing, the synthesis continued with the sequence following Fmoc-amino acid activation and coupling steps.

Cleavage and deprotection. Cleavage and total deprotection of the synthesized peptides were carried out in 95% trifluoroacetic acid (TFA) containing 2.5% triisopropylsilane (TIS) and 2.5% water. 200 mg of the resin was treated with 2 ml of the cleavage cocktail for 2 hours. The peptides were precipitated with 10 volumes of cold diethyl ether, the resin was washed twice with 0.1 volumes of TFA, added to the ether, mixed, and centrifuged. The pellet was washed twice with the same volume of diethyl ether. The peptides were dried in vacuum, weighed, and analyzed by HPLC.

HPLC analysis. Crude peptides were analyzed on an Ettan LC HPLC instrument by using an YMC C18 column (3.5 µm, 100 Å, 50×2.1 mm). HPLC solvents were—A: 0.1% TFA/water, and B: 95% acetonitrile/water/0.1% TFA. A gradient 20-40% B over 15 min was employed. Absorbance was monitored at 214 nm.

Results.

Figure 5:
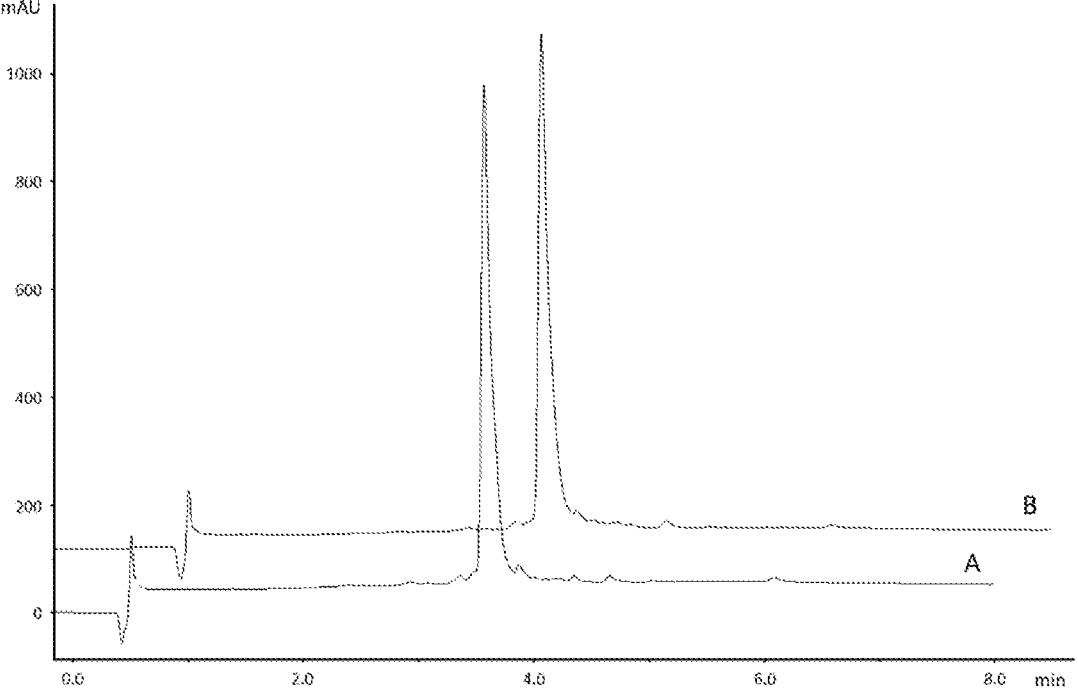
FIG. 5. is RP-HPLC analysis chromatograms of peptides from one example of the invention.

FIG. 5 shows comparative RP-HPLC analysis after synthesis of Bivalirudin analogue FPRPGGGGNGDFEE-IPEEYL-amide using different modes of activation (A and B). DIC/OxymaPure was used in both syntheses. A) Fmoc-amino acids were pre-activated in the separate mixing chamber (calculated purity of crude peptide 93%, yield 75%); B) Fmoc-amino acids were in-line activated directly in the column (calculated purity of crude peptide 92%, yield 72%).

Figure 6:
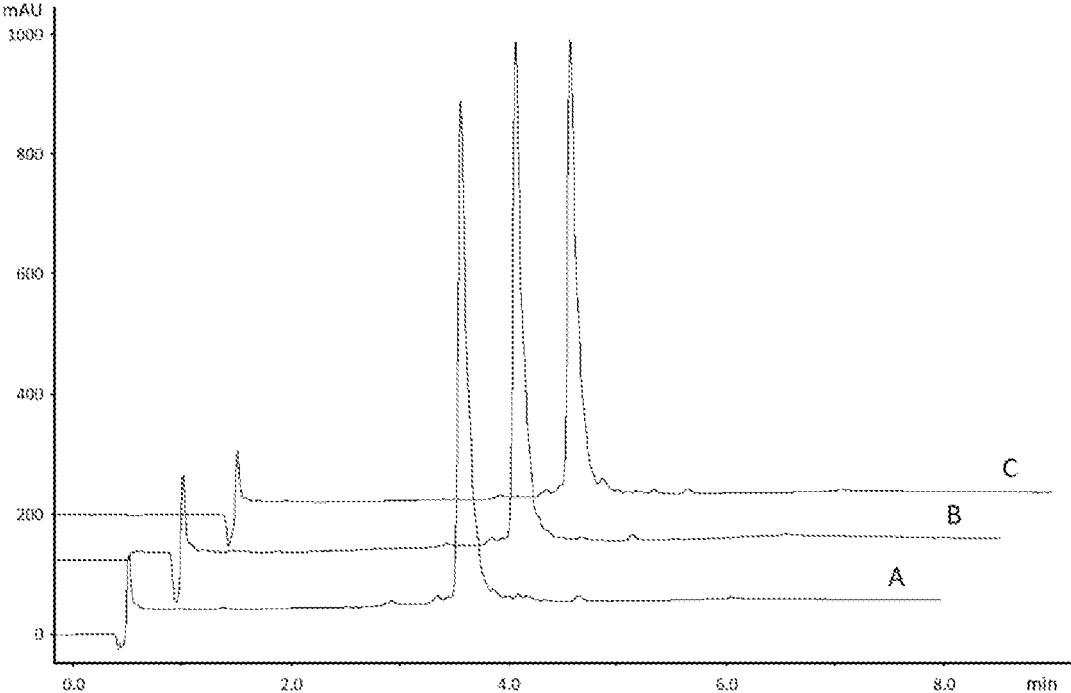
FIG. 6. is RP-HPLC analysis chromatograms of peptides from one example of the invention.

FIG. 6 shows comparative RP-HPLC analysis after synthesis of Bivalirudin analogue FPRPGGGGNGDFEE-IPEEYL-amide using different coupling times (A: 10 min, B: 20 min, and C: 40 min). DIC/OxymaPure was used in all syntheses and Fmoc-amino acids were preactivated in the separate mixing chamber at ambient temperature for 5 min.

The following results were obtained using different coupling times:

coupling time 10 min (A)—purity 94%, yield 66%;
coupling time 20 min (B)—purity 94%, yield 76%; and
coupling time 40 min (C)—purity 93%, yield 75%.

Example 2

Synthesized peptide. An N-terminal fragment of peptide hormone Secretin, Secretin(1-13), having the amino acid sequence HSDGTFTSELSRL, where each letter denotes a one-letter code for amino acids, was synthesized with a C-terminal amide group.

Preparation and attachment of reagents to the system. Containers containing solutions made up in N,N-dimethylformamide (DMF) of Fmoc-amino acids (0.5 M), coupling reagent (1.0 M N,N'-diisopropylcarbodiimide, DIC), and additive (0.5 M ethyl cyano(hydroxyimino)acetate, Oxyma-Pure) were connected to the synthesizer. The solvent DMF was connected to the system at its dedicated inlet. 20% piperidine (v/v) and capping reagent (0.3 M acetic anhydride combined with 0.3 M pyridine) were prepared in DMF, and were connected to their predetermined inlets. All inlets were purged to eliminate gas/air from the tubings and to fill the tubings with the corresponding solutions or solvents.

Heater (i.e. temperature regulating device). The temperature of the heater was set to achieve 43° C. in the column during recirculation at the coupling step. The pre-activation step was carried out at ambient temperature, by-passing the heater. Fmoc-amino acid coupling, Fmoc-group de-blocking steps, and subsequent column washes were carried out by using solutions passing through the heater.

Preparation of the column reactor. The column reactor was prepared as described for Example 1 above.

Synthesis using pre-activation in a separately defined mixing chamber and coupling of activated amino acids. The indicated number of equivalents of 0.5 M Fmoc-amino acid solution was pumped from the amino acid container into the mixer, followed by equal number of equivalents of 0.5 M OxymaPure solution and three times larger number of equivalents of 1.0 M DIC solution. The reagents were mixed in the mixing chamber by recirculation at a flowrate of 30 ml/min for 5 min at room temperature, by-passing both the column and the heater. The activated amino acid was pumped from the mixer into the column through the heater. Pumping was monitored by UV- and gas bubble detectors. The mixture was then recirculated for a pre-determined time through the column at flowrate 100-200 cm/h, followed by capping.

Synthesis using straight-through flow in coupling (single pass through the column). In these experiments 2 or 4 equivalents of 0.5 M Fmoc-amino acid solution in DMF was mixed with the same amount of OxymaPure solution and 6 or 12 equivalents of 1.0 M DIC solution, respectively. Fmoc-amino acid was preactivated for 5 minutes and pumped through the 25 ml synthesis column containing the resin (2.777 g, loading 0.41 mmol/g). For the experiment with 2 equivalents a flow rate of 4 cm/h was used and for the experiment with 4 equivalents the flow rate was 8 cm/h.

After emptying of the mixer, the flow was continued with DMF, which was applied for 1.5 column volumes followed by capping.

Capping. The amino acid coupling step was followed by capping using 0.3 M acetic anhydride and 0.3 M pyridine in DMF. One column volume of capping solution was pumped through the column followed by 1.3 column volumes of DMF. Contact time of the capping solution with the resin was 5 min. The progress of the capping and subsequent washing was monitored by UV detection.

Fmoc-group removal. The procedure was carried out as described for Example 1.

Mixer washing. Mixer washes were done as described for Example 1.

Cleavage and deprotection. Cleavage and total deprotection of the synthesized peptides were carried out in 95% trifluoroacetic acid (TFA) containing 2.5% triisopropylsilane (TIS) and 2.5% water. 200 mg of the resin was treated with 2 ml of the cleavage cocktail for 2 hours. The peptides were precipitated with 10 volumes of cold diethyl ether, the resin was washed twice with 0.1 volumes of TFA, added to the ether, mixed, and centrifuged. The pellet was washed twice with the same volume of diethyl ether. The peptides were dried in vacuum, weighed, and analyzed by HPLC.

HPLC analysis. Crude peptides were analyzed on an Agilent 1100 Series HPLC instrument by using a Phenomenex Aeris C18 column (2.6 μm, 100 Å, 150×2.1 mm) equipped with a guard column at 50° C. HPLC solvents were—A: 0.1% TFA/water, and B: 70% acetonitrile/water/ 0.1% TFA. A gradient 20-57% B over 30 min was employed. Absorbance was monitored at 214 nm.

Results.

Figure 7:
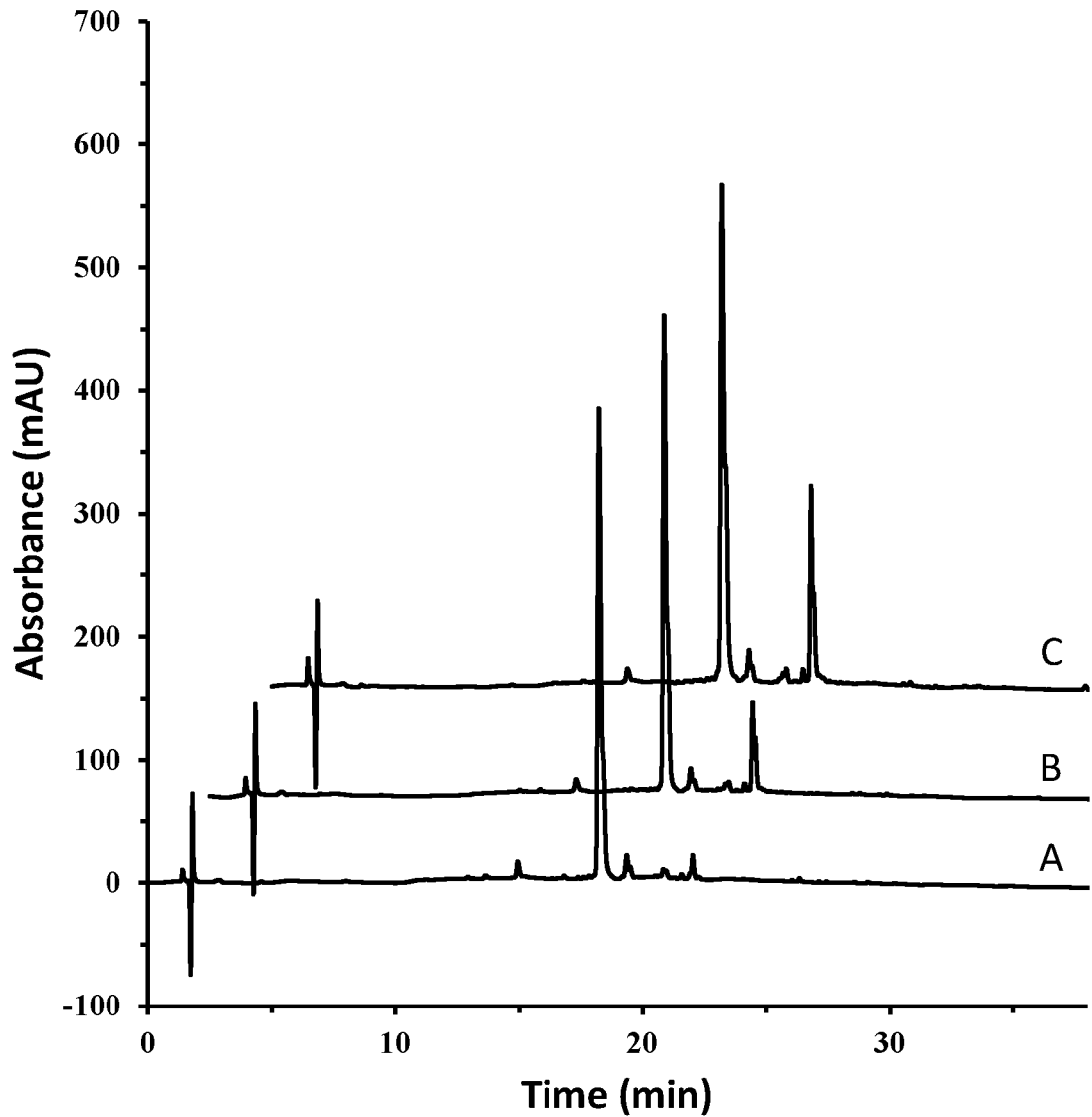
FIG. 7. is RP-HPLC analysis chromatograms of peptides from one example of the invention.

FIG. 7 shows HPLC analysis of Secretin(1-13) synthesized by recirculation of activated Fmoc-amino acids in the column (A), and by a single pass of the coupling mixture through the column by using 4 equivalents of Fmoc-amino acids (B) and by using 2 equivalents (C). The synthesis scale was 1.139 mmol (25 ml column), recirculation time was 40 min for A, flowrate 150 cm/h. Flowrates for single pass couplings were 1.3 ml/min for B and 0.6 ml/min for C. Calculated yields and purities of the synthesized peptides are given in Table 1 below.

TABLE 1

| Yields and purities for HPLC curves A-C in FIG. 7. | | | | | |
|---|---|---|---|---|---|
| HPLC curve | Coupling mode | Scale equiv- alents | Yield by resin weight gain, % | Yield from cleavage, % | Purity by HPLC, % |
| A | Recirculation | 2.0 | 103 | 93 | 85.7 |
| B | Single pass | 4.0 | 89 | 75 | 74.1 |
| C | Single pass | 2.0 | 86 | 72 | 63.7 |

It can be concluded that recirculation in the column leads to higher purity and higher yield compared to a single pass coupling using the same amount of Fmoc-amino acid equivalents. Single pass couplings using 4 equivalents of amino acids leads to higher purity and yield compared to using 2 equivalents.

Figure 8:
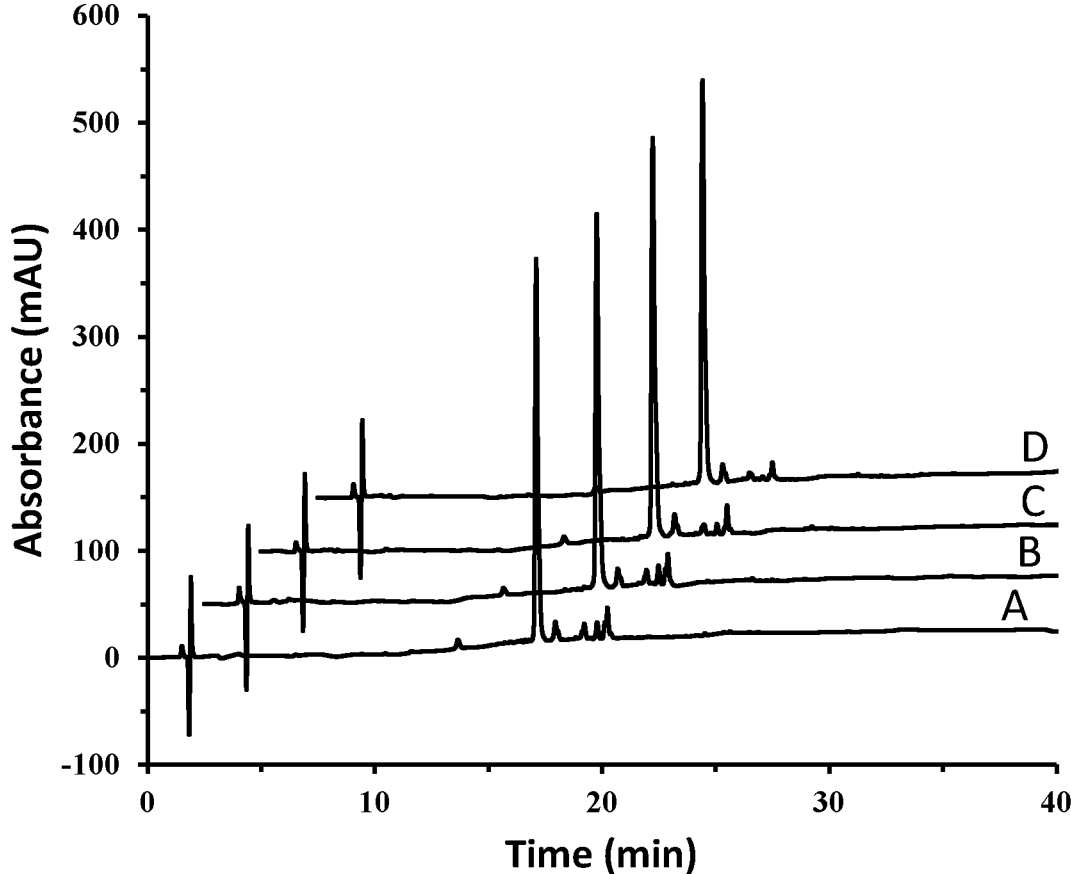
FIG. 8. is RP-HPLC analysis chromatograms of peptides from one example of the invention.

FIG. 8 shows comparative RP-HPLC analysis of Secretin (1-13)-amide (HSDGTFTSELSRL-amide) synthesized using different numbers of amino acid equivalents of the synthesis scale (1.138 mmol; 25 ml column). Calculated yields and purities of the synthesized peptides are given in Table 2 below.

TABLE 2

| | | Yields and purities for HPLC curves A-D in FIG. 8. | | |
| --- | --- | --- | --- | --- |
| HPLC curve | Scale equivalents | Yield by resin weight gain, % | Yield from cleavage, % | Purity by HPLC, % |
| A | 1.1 | 92 | 97 | 77.5 |
| B | 1.2 | 95 | 77 | 76.0 |
| C | 1.3 | 98 | 86 | 82.6 |
| D | 2.0 | 103 | 93 | 85.7 |

It can be concluded that with the system described peptide synthesis can be carried out with high efficiency using low amounts of amino acid equivalents, such as 2 equivalents, 1.3 equivalents, 1.2 equivalents, or even 1.1 equivalents. Synthesis with the system results in high yield and high purity of peptides.

Figure 9:
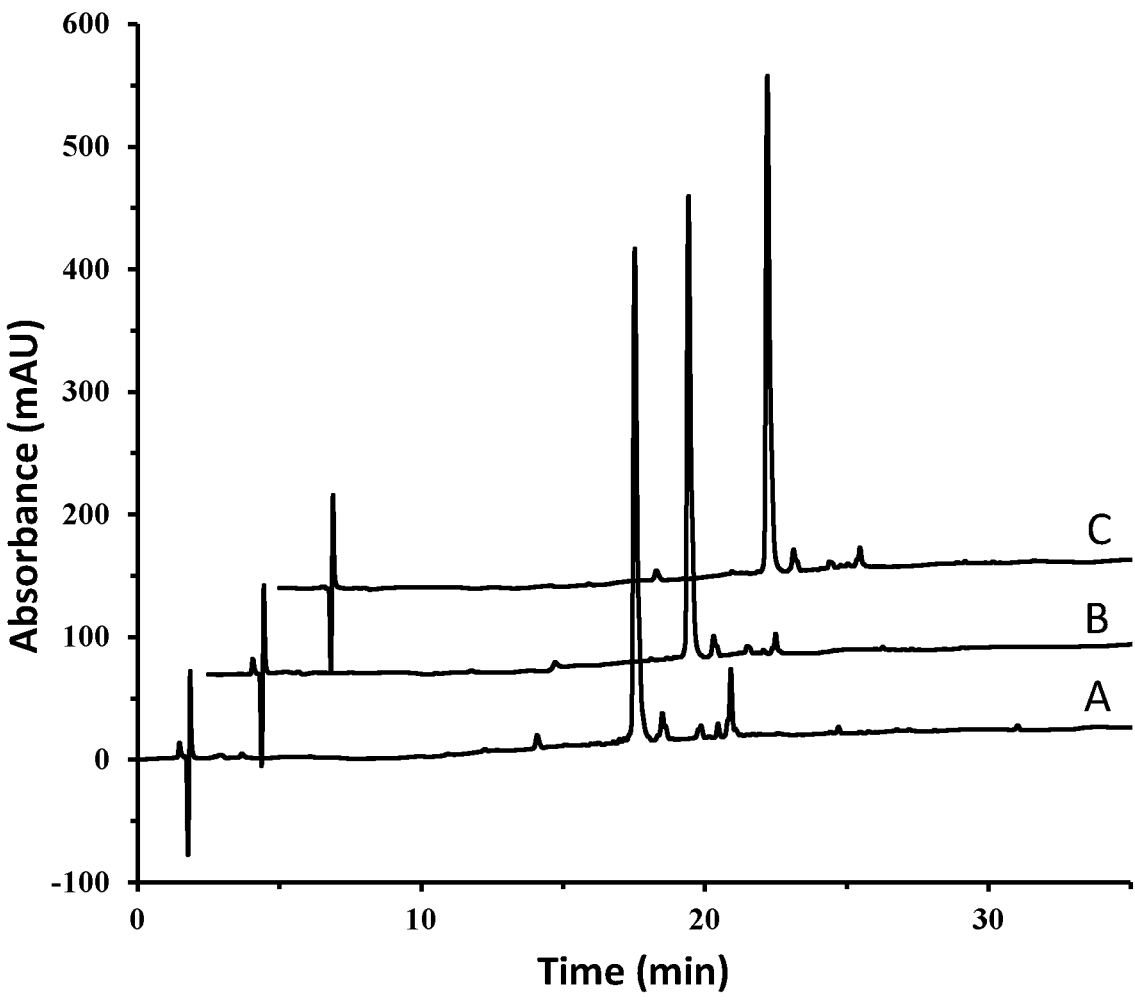
FIG. 9. is RP-HPLC analysis chromatograms of peptides from one example of the invention.

FIG. 9 shows HPLC analysis of Secretin(1-13) synthesized at different scales. A) 0.570 mmol in 12.5 ml column; B) 1.138 mmol in 25 ml column; C) 2,277 mmol in 50 ml column. Scale equivalents of Fmoc-amino acids were 2.0. Calculated yields and purities of the synthesized peptides are given in Table 2 below.

TABLE 2

| | | Yields and purities for HPLC curves A-C in FIG. 9. | | |
| --- | --- | --- | --- | --- |
| HPLC curve | Synthesis scale | Yield by resin weight gain, % | Yield from cleavage, % | Purity by HPLC, % |
| A | 0.570 | 103 | 94 | 80.7 |
| B | 1.138 | 103 | 93 | 85.7 |
| C | 2.277 | 105 | 87 | 85.9 |

It can be concluded that peptide synthesis carried out using the system is scalable leading to similar results independent of the scale.

The invention claimed is:

1. A flow-through process for solid phase peptide synthesis (SPPS) including cyclic addition of at least one amino acid to a column packed with resin, wherein each cycle includes the combination of amino acid(s) with one or more reagents to provide an amino acid mixture which is passed through the column, which method comprises:

heating the amino acid mixture before being passed through the column;

passing the amino acid mixture through the column packed with resin; and recirculating the amino acid mixture at least once over the column packed with resin;

wherein, in each cycle, peptides are synthesized by linking at least one amino acid from the mixture to at least one amino acid immobilized to the resin; and wherein the heated amino acid mixture is passed through the column at a flow rate and in a volume that allow for their contact with at least 99% of immobilized and growing peptides.

2. The process according to claim 1, wherein the amino acid(s) are combined with said reagent(s) in a separately defined mixing chamber.

3. The process according to claim 1, wherein the amino acid(s) are combined with said reagent(s) in the tubing of the system.

4. The process according to claim 1, wherein the amino acid(s) are combined with said reagent(s) in the column packed with resin.

5. The process according to claim 1, wherein the number of equivalents of amino acids is ≤3.

6. The process according to claim 2, wherein the mixing chamber is emptied and cleaned between the cycles and wherein progress of the cleaning is monitored by a UV/visible/IR light detector, or fluorescence detector, or a conductivity detector or both.

7. The process according to claim 1, wherein the reagents comprise at least one activating agent and the amino acids are in-line activated in the tubing or in the column.

8. The process according to claim 2, wherein the reagents comprise at least one activating agent and the amino acids are pre-activated in the mixing chamber while the column resin is being de-blocked and/or washed.

9. The process according to claim 2, wherein the outflow of the mixing chamber is monitored using gas bubble detection.

10. The process according to claim 1, wherein the column is thermally insulated.

11. The process according to claim 1, wherein the volume without resin in the column is more than about 1% of the column volume.

12. The process according to claim 1, wherein progress of the peptide synthesis in the column is continuously monitored using at least one detector.

13. The process according to claim 12, wherein the at least one detector is a UV/Vis light detector, fluorescence detector, an NIR detector, a mass spectrometry detector or a conductivity detector.

14. The process according to claim 13, wherein the at least one detector is a UV/Vis light detector and the light can be detected simultaneously at least at four different wavelengths.

15. The process according to claim 1, wherein the process uses software controlled real-time conditional monitoring that enables the use of Process Analytical Technology (PAT) to measure Critical Process Parameters (CPP) which affect Critical Quality Attributes (CQA).

16. The process according to claim 1, where the process is preceded by wetting of the resin packed in the column prior to or during combining the amino acid(s) with one or more reagents.

17. The process according to claim 1, wherein the process uses software controlled real-time conditional monitoring of critical parameters.

18. The process according to claim 5, wherein the number of equivalents of amino acids is ≤2.

* * * * *